United States Patent
Clemente et al.

(10) Patent No.: US 9,737,655 B2
(45) Date of Patent: Aug. 22, 2017

(54) INTEGRATED PIERCEABLE SEAL FLUID PATHWAY CONNECTION AND DRUG CONTAINERS FOR DRUG DELIVERY PUMPS

(71) Applicant: UNITRACT SYRINGE PTY LTD, Sydney (AU)

(72) Inventors: Matthew J. Clemente, Downington, PA (US); Ian B. Hanson, Wayne, PA (US); Paul F. Bente, IV, Wayne, PA (US)

(73) Assignee: UNITRACT SYRINGE PTY LTD, Sydney (AU)

( * ) Notice: Subject to any disclaimer, the term of this patent is extended or adjusted under 35 U.S.C. 154(b) by 48 days.

(21) Appl. No.: 14/466,403

(22) Filed: Aug. 22, 2014

(65) Prior Publication Data

US 2015/0057613 A1     Feb. 26, 2015

Related U.S. Application Data

(60) Provisional application No. 61/869,192, filed on Aug. 23, 2013.

(51) Int. Cl.
*A61M 5/142* (2006.01)
*A61M 39/10* (2006.01)
(Continued)

(52) U.S. Cl.
CPC .... *A61M 5/14224* (2013.01); *A61M 5/14244* (2013.01); *A61M 5/14248* (2013.01);
(Continued)

(58) Field of Classification Search
CPC .......... A61M 5/14224; A61M 5/14566; A61M 2005/14252; A61M 39/16; A61M 39/18; A61M 2039/1066; A61M 2039/1072
See application file for complete search history.

(56) References Cited

U.S. PATENT DOCUMENTS 4,004,586 A   1/1977   Christensen et al.
4,548,606 A   10/1985   Larkin
(Continued)

FOREIGN PATENT DOCUMENTS

CN    101557847    10/2009
CN    101631585    1/2010
(Continued)

OTHER PUBLICATIONS

International Search Report and Written Opinion, mailed Dec. 18, 2014, in related International Application No. PCT/US2014/052329, filed Aug. 22, 2014.
(Continued)

*Primary Examiner* — Laura Bouchelle
*Assistant Examiner* — Justin L Zamory
(74) *Attorney, Agent, or Firm* — Wiley Rein LLP

(57) ABSTRACT

A sterile fluid pathway connector includes a piercing member, a connector hub, and a pierceable seal; wherein at least a portion of the pierceable seal is configured to move from a first position in which the piercing member is retained within a sterile cavity between the pierceable seal and the connector hub, to a second position in which the pierceable seal has been penetrated by the piercing member. A filter may be utilized to enclose the sterile cavity from the outside environment. Such fluid pathway connections may be integrated into a fluid container having a barrel and a plunger seal. The components of the fluid pathway connector may further be capable of transmitting a signal to the user upon completion of fluid delivery, for example, upon contact between the plunger seal and the pierceable seal. A fluid delivery pump includes such integrated fluid pathway connectors and fluid containers.

13 Claims, 22 Drawing Sheets

(51) Int. Cl.
　　　*A61M 39/18*　　(2006.01)
　　　*A61M 5/145*　　(2006.01)

(52) U.S. Cl.
　　　CPC ........ *A61M 5/14566* (2013.01); *A61M 39/10* (2013.01); *A61M 39/18* (2013.01); *A61M 2039/1072* (2013.01)

(56) References Cited

U.S. PATENT DOCUMENTS

| | | |
|---|---|---|
| 4,565,543 A | 1/1986 | Bekkering |
| 4,673,400 A | 6/1987 | Martin |
| 4,685,903 A | 8/1987 | Cable et al. |
| 4,755,173 A | 7/1988 | Konopka et al. |
| 4,840,620 A | 6/1989 | Kobayashi et al. |
| 5,167,816 A | 12/1992 | Kruger et al. |
| 5,616,132 A | 4/1997 | Newman |
| 5,795,339 A | 8/1998 | Erskine |
| 5,858,001 A | 1/1999 | Tsals et al. |
| 6,248,093 B1 | 6/2001 | Moberg |
| 6,699,218 B2 | 3/2004 | Flaherty et al. |
| 7,063,684 B2 | 6/2006 | Moberg |
| D564,087 S | 3/2008 | Yodfat |
| D585,543 S | 1/2009 | Yodfat |
| 7,479,135 B2 | 1/2009 | Richter et al. |
| 7,611,503 B2 | 11/2009 | Spohn et al. |
| 7,780,636 B2 | 8/2010 | Radmer |
| 7,803,134 B2 | 9/2010 | Sharifi et al. |
| 7,846,132 B2 | 12/2010 | Gravesen et al. |
| 7,879,010 B2 | 2/2011 | Hunn |
| 7,905,859 B2 | 3/2011 | Bynum et al. |
| 7,927,306 B2 | 4/2011 | Cross |
| 7,967,795 B1 | 6/2011 | Cabiri |
| 8,029,472 B2 | 10/2011 | Leinsing et al. |
| 8,048,031 B2 | 11/2011 | Shaw et al. |
| 8,152,771 B2 | 4/2012 | Mogensen |
| 8,157,769 B2 | 4/2012 | Cabiri |
| 8,162,892 B2 | 4/2012 | Mogensen |
| 8,167,844 B2 | 5/2012 | Dillard, III |
| 8,187,232 B2 | 5/2012 | Chong et al. |
| D669,165 S | 10/2012 | Estes |
| 8,409,145 B2 | 4/2013 | Raymond |
| D684,685 S | 6/2013 | Schneider |
| D684,686 S | 6/2013 | Cronenberg |
| D685,083 S | 6/2013 | Schneider |
| 8,465,455 B2 | 6/2013 | Cabiri |
| 8,591,465 B2 | 11/2013 | Hommann |
| 8,597,256 B2 | 12/2013 | Lanin |
| D709,183 S | 7/2014 | Kemlein |
| 8,795,234 B2 | 8/2014 | Kadamus |
| D723,157 S | 2/2015 | Clemente |
| 9,005,169 B2 | 4/2015 | Gravesen |
| D745,142 S | 12/2015 | O'Connor |
| D752,442 S | 3/2016 | O'Donahue |
| 9,463,280 B2 | 10/2016 | Cabiri |
| 2004/0092878 A1 | 5/2004 | Flaherty |
| 2007/0010789 A1 | 1/2007 | Peter et al. |
| 2007/0179444 A1 | 8/2007 | Causey |
| 2008/0132842 A1 | 6/2008 | Flaherty |
| 2008/0269687 A1 | 10/2008 | Chong |
| 2009/0124979 A1 | 5/2009 | Raymond et al. |
| 2009/0204077 A1 | 8/2009 | Hasted et al. |
| 2009/0240240 A1 | 9/2009 | Hines |
| 2011/0098652 A1 | 4/2011 | Hasted et al. |
| 2011/0166509 A1 | 7/2011 | Gross et al. |
| 2012/0035546 A1 | 2/2012 | Cabiri |
| 2012/0096953 A1 | 4/2012 | Bente, IV |
| 2012/0123354 A1 | 5/2012 | Woehr |
| 2013/0060196 A1 | 3/2013 | O'Connor |
| 2013/0066274 A1* | 3/2013 | O'Connor ........... A61M 5/1452 604/151 |
| 2013/0131595 A1 | 5/2013 | Ekman |
| 2014/0213975 A1 | 7/2014 | Clemente |
| 2014/0238542 A1 | 8/2014 | Kvale |

FOREIGN PATENT DOCUMENTS

| | | |
|---|---|---|
| EP | 1702635 A2 | 9/2006 |
| EP | 1341569 B1 | 1/2007 |
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2269559 | 1/2011 |
| EP | 2379134 A1 | 10/2011 |
| EP | 2429612 A1 | 3/2012 |
| EP | 2433663 A1 | 3/2012 |
| JP | 2004-195227 | 7/2004 |
| JP | 2004-528939 | 9/2004 |
| JP | 2010-501211 | 1/2010 |
| JP | 2010-501281 | 1/2010 |
| JP | 2010-531196 | 9/2010 |
| JP | 2010-538751 | 12/2010 |
| JP | 2011-045537 | 3/2011 |
| WO | 95/19194 | 7/1995 |
| WO | 99/48546 A1 | 9/1999 |
| WO | 03/024504 A2 | 3/2003 |
| WO | 03/103763 A1 | 12/2003 |
| WO | 2004/035116 | 4/2004 |
| WO | 2004/062714 A1 | 7/2004 |
| WO | 2005/037350 A2 | 4/2005 |
| WO | 2005/044344 | 5/2005 |
| WO | 2006/129196 | 12/2006 |
| WO | 2008/024808 A2 | 2/2008 |
| WO | 2008/133702 | 11/2008 |
| WO | 2010/029054 A1 | 3/2010 |
| WO | 2010/077807 A1 | 7/2010 |
| WO | 2010/084113 A1 | 7/2010 |
| WO | 2010/085338 | 7/2010 |
| WO | 2010/112377 | 10/2010 |
| WO | 2010/112377 A1 | 10/2010 |
| WO | 2010/132196 A1 | 11/2010 |
| WO | 2011/006652 | 1/2011 |
| WO | 2011/006652 A1 | 1/2011 |
| WO | 2011/046950 | 4/2011 |
| WO | 2011/090956 A1 | 7/2011 |
| WO | 2011/121023 A1 | 10/2011 |
| WO | 2012/032411 A2 | 3/2012 |
| WO | 2012/131044 A1 | 10/2012 |
| WO | 2013/033467 | 3/2013 |
| WO | 2013/156224 | 10/2013 |

OTHER PUBLICATIONS

International Search Report and Written Opinion mailed, on Feb. 28, 2013, in PCT/US2012/053241, filed Aug. 30, 2012.

International Search Report and Written Opinion mailed, on Mar. 28, 2013, in PCT/US2012/053174, filed Aug. 30, 2012.

International Search Report and Written Opinion mailed, Feb. 18, 2013, in PCT/US2012/05481, filed Sep. 12, 2012.

Preliminary Amendment and Application Data Sheet filed on Jul. 9, 2012 in U.S. Appl. No. 13/521,181, filed Jul. 9, 2012.

European Patent Office, Communication Relating to the Results of the Partial International Search in International Application No. PCT/US2012/053241, 2 pages (Nov. 30, 2012).

European Patent Office, International Search Report in International Patent Application No. PCT/US2012/054861, 8 pages (Feb. 18, 2013).

European Patent Office, Written Opinion of the International Searching Authority in International Application No. PCT/US2012/053174, 6 pages (Mar. 28, 2013).

European Patent Office, Written Opinion of the International Searching Authority in International Application No. PCT/US2012/053241, 8 pages (Feb. 28, 2013).

Preliminary Amendment and Application Data Sheet Filed in National Phase of WO2011/090956 A2 (U.S. Appl. No. 13/521,181) (Jul. 9, 2012).

(56) References Cited

OTHER PUBLICATIONS

European Patent Office, International Search Report and Written Opinion in International Patent Application No. PCT/US2013/030478, 11 pages (Nov. 18, 2013).

* cited by examiner

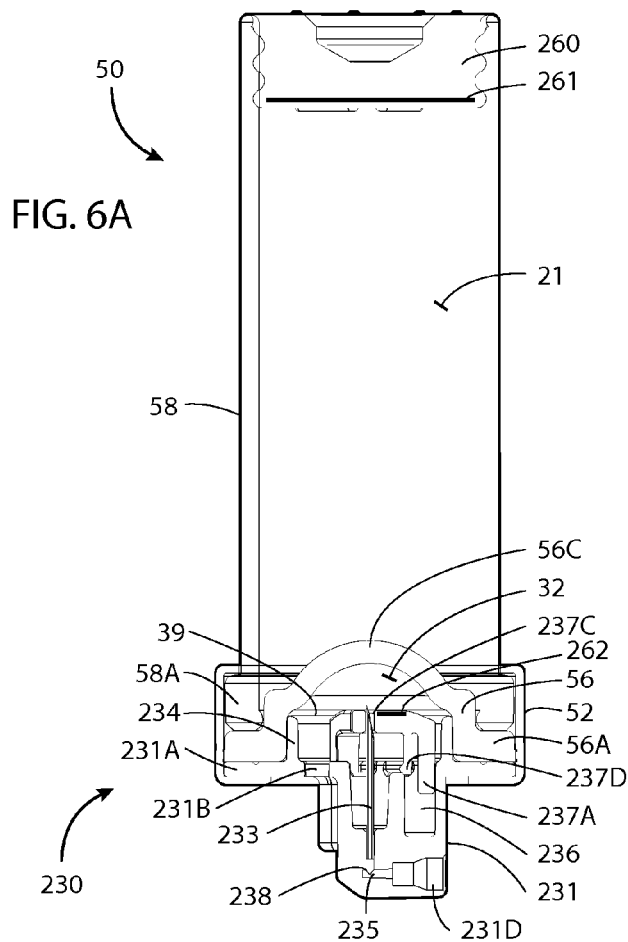
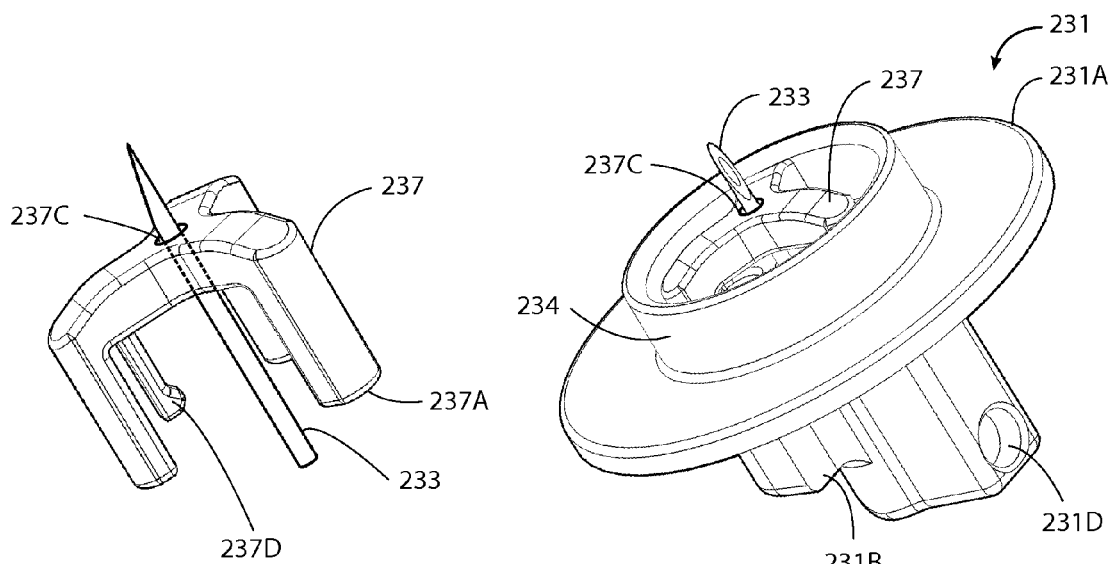

INTEGRATED PIERCEABLE SEAL FLUID PATHWAY CONNECTION AND DRUG CONTAINERS FOR DRUG DELIVERY PUMPS

RELATED APPLICATION

This application claims priority benefit of U.S. Application No. 61/869,192, filed 23 Aug. 2013, which is incorporated herein by reference for all purposes.

FIELD

The embodiments described herein relate to drug delivery pumps. More particularly, these embodiments relate to fluid pathway connections that are integrated into or at least partially within drug containers, drug delivery pumps that utilize these connections, the methods of operating such devices, and the methods of assembling such devices.

BACKGROUND

Parenteral delivery of various drugs has become a desired method of drug delivery for a number of reasons. Drug delivery by injection may enhance the effect of the substance being delivered and ensure that the unaltered medicine reaches its intended site at a significant concentration. Additionally, undesired side effects associated with other routes of delivery, such as systemic toxicity, may be minimized through parenteral delivery. Bypassing the digestive system of a mammalian subject avoids digestive degradation, absorption difficulties and first-pass metabolism issues, thereby enhancing delivery of a necessary amount of drug, at a desired concentration, to the targeted site.

Traditionally, manually operated syringes and injection pens have been employed for delivering parenteral drugs to a patient. More recently, the parenteral delivery of liquid medicines has been accomplished by several means, including bolus injections that use a needle and a reservoir, gravity driven dispensers, or transdermal patch technologies. Bolus injections often imperfectly match the clinical needs of the patient, however, and usually require larger individual doses than are desired at the specific time of administration. Continuous delivery of medicine through gravity-feed systems may compromise a patient's mobility and lifestyle, and may limit the therapy to simplistic flow rates and profiles. Transdermal patches also have restrictions in requiring specific molecular drug structures for efficacy, and the control of the drug administration through a transdermal patch is often severely limited.

Compared to these approaches to parenteral administration, pump type delivery devices (e.g., ambulatory infusion pumps), can be significantly more convenient for patients, because drug doses may be calculated and delivered automatically to a patient at any time during the day or night. Further, when used in conjunction with metabolic sensors or monitors, pumps can be controlled automatically to provide need-based doses of a fluidic medium based on sensed or monitored metabolic levels. These infusion devices may thus offer sophisticated fluid delivery profiles, accomplishing bolus requirements, continuous infusion and variable flow rate delivery. The infusion capabilities usually result in better efficacy of the drug and therapy and less toxicity. As a result, infusion devices have become an important aspect of modern medical treatments of various types of medical conditions, such as diabetes.

Unfortunately, many current ambulatory infusion devices are expensive, difficult to program and prepare for infusion; and tend to be bulky, heavy and fragile. Additionally, filling these devices can often be difficult, and require the patient to carry both the intended medication as well as filling accessories. These devices often require specialized care, maintenance, and cleaning to assure proper function and safety for their intended long-term use, and are not cost-effective for patients or healthcare providers. Hence, although pump type delivery systems have been used to solve a number of patient needs, manually operated syringes and injection pens still remain a preferred choice for drug delivery because they provide integrated safety features, and can more easily identify the status of drug delivery such as the end of dose dispensing. Manually operated syringes and injections pens are not universally applicable, however, and are not preferred for delivery of all drugs. Therefore, there remains a need for an adjustable, or programmable, infusion system that is precise and reliable and can offer clinicians and patients a small, low cost, light weight, simple to use alternative for parenteral delivery of liquid medicines.

SUMMARY

The present embodiments provide for container connections that maintain the sterility of a fluid pathway and are integrated into a fluid container; fluid delivery pumps that incorporate such sterile fluid pathway connections to fluid containers; methods of operating such devices; and methods of assembling such devices. The fluid pathway connections of the present embodiments provide integrated safety features that ensure the sterility of the fluid pathway before, during, and after fluid delivery. In one aspect, the fluid pathway remains disconnected from the fluid container until the device has been initiated by the operator. In another aspect, the fluid pathway maintains the sterility of a piercing member prior to connection with the fluid container within a sterile cavity prior to activation by the operator. Upon activation by the operator, at least a portion of a pierceable seal is translated, such as by pneumatic and/or hydraulic pressure or force within the fluid, towards a substantially fixed piercing member such that the pierceable seal is pierced and the fluid pathway is connected or opened to enable fluid flow through the fluid pathway for fluid delivery from the device. Accordingly, the novel devices of the present invention alleviate one or more of the problems associated with prior art devices, such as those referred to above.

A drug pump, such as an infusion pump or a bolus injector, may be needed to deliver a particular amount of fluid within a period of time. For example, when delivering a drug fluid subcutaneously it is important to control the flow of fluid that is delivered into the patient and to maintain the sterility of the fluid container and fluid pathway prior to activation or operation of the fluid delivery device. It may be desired that the fluid pathway connection remains disconnected, for container integrity, sterility, and other purposes, until the user has activated the device and initiated fluid flow from a container. Some fluid pump systems may utilize one or more active fluid pathway control mechanisms to prevent premature fluid pathway connection or drug delivery. Other fluid pump systems are configured such that fluid pathway connection is made upon manufacture, and fluid delivery is blocked until desired by the user. Such designs do not provide the beneficial advantages associated with maintaining container integrity and sterility of the internal components of the drug delivery device. The present embodiments provide an integrated fluid pathway connection mechanism for sterile fluid delivery pumps. These novel embodiments provide both a connection mechanism to open or connect a sterile fluid pathway between a fluid container and a fluid conduit, without adding unnecessary steps for the user. This is enabled by activation of the drive mechanism and translation of the plunger seal, resulting in pneumatic and/or hydraulic pressure within the fluid that forces translation of at least a portion of a pierceable seal, causing it to impact upon a substantially stationary piercing member, thus opening a sterile fluid pathway between the fluid container and the fluid conduit.

Accordingly, the embodiments of the present invention provide a sterile fluid pathway connection that is integrated into a fluid container and opened, connected, activated, or otherwise enabled by the operation of the device and drive mechanism. The activation of the drive mechanism and the force transferred from the drive mechanism to the plunger seal is, itself, used to open a sterile fluid pathway between the fluid container and the fluid conduit. Accordingly, container integrity and sterility of the fluid container may be maintained prior to and during operation of the device. This novel configuration also automates the sterile fluid pathway connection step, greatly reducing the complexity of the device and operational steps needed to be performed by the device or the user. The novel embodiments of the present invention also permit flexibility in device component configurations, and reduce the layout or overall footprint of the device because no separate sterile fluid pathway connection mechanism is needed on the cap-side of the fluid container. The present embodiment may also be implemented fully or utilized in standard production of sterile fluids, including drug fill-finish processes, including applications that require the pulling of a vacuum. Additionally, the present embodiments may also integrate a number of different status indication mechanisms into the device, including utilizing the piercing member or the plunger seal as parts of an indication mechanism that relates status of fluid transfer from the sterile fluid container to the connector. For example, when the fluid container is a drug container, such components and devices provide an end-of-dose indication coupled to the actual travel and drug delivery status of the plunger seal.

At least one embodiment provides for a sterile fluid pathway connection that includes a piercing member, a connector hub, and a pierceable seal. More specifically, at least one embodiment provides for sterile fluid connector comprising a first portion configured to connect a sterile fluid pathway and a second portion comprising a housing configured to mount a sterile fluid container; a connector hub; a pierceable seal disposed at least partially between the connector hub and the sterile fluid container and forming a sterile fluid chamber between the connector hub and the pierceable seal; and a piercing member disposed within the connector hub capable of providing a sterile fluid communication between the sterile fluid chamber and the sterile fluid pathway; wherein at least a portion of the pierceable seal is configured to transform from a non-activated state in which the pierceable seal is intact, to an activated state in which the pierceable seal is disrupted by the piercing member to create a sterile fluid communication between the sterile fluid container and the sterile fluid pathway. The housing may be further configured to recess a portion of the connector within the sterile fluid container. The connector hub may further comprise at least one port or vent. The sterile fluid pathway may also include at least one sensor configured to indicate the status of fluid transfer from the sterile fluid container to the connector. Additionally, the sterile fluid pathway connector may include one or more flow restrictors. In at least one embodiment, the connector hub may at least partially function as a fluid conduit or flow restrictor. In at least one embodiment, the fluid pathway connection further includes a filter. A number of known filters may be utilized within the embodiments of the present invention, which would readily be appreciated by an ordinarily skilled artisan. For example, the filter may comprise a permeable membrane, semi-permeable membrane or porous membrane, which encloses the sterile cavity from the outside environment.

The piercing member is initially retained in a substantially fixed position within a sterile cavity between the connector hub and the pierceable seal. Upon activation by the operator (e.g., a patient), at least a portion of the pierceable seal is caused to move to a second position in which the pierceable seal is penetrated by the piercing member. Force, such as pneumatic and/or hydraulic force, applied on the pierceable seal on the side opposing the sterile cavity, causes translation of at least a portion of the pierceable seal towards the piercing member. The translation of the pierceable seal causes it to impact upon the substantially stationary or fixed piercing member to open a fluid pathway through the pierceable seal. Accordingly, at least a portion of the pierceable seal is configured to move from the first position to the second position by force applied by a fluid on the pierceable seal. Penetration by the piercing member of the pierceable seal upon movement of a portion of the pierceable seal from the first position to the second position opens a fluid pathway through the pierceable seal and the piercing member to a fluid conduit.

In at least one embodiment, the pierceable seal comprises a seal barrier that can be penetrated by the piercing member. The piercing member may initially be in contact with, or adjacent to, the seal barrier.

The fluid pathway connection may further include a piercing member guide, wherein the piercing member guide is capable of engaging with or translating upon the connector hub. The piercing member guide may function to ensure that the pierceable seal, or at least a portion thereof such as a seal barrier, properly contacts the piercing member and translates thereupon to become pierced and open the fluid pathway through the pierceable seal and piercing member to a fluid conduit.

The piercing member may be configured to pass into the connector hub and connect to a fluid conduit. In another embodiment, the connector hub may connect the piercing member to the fluid conduit, and the fluid conduit may be at least partially a part of the connector hub. In at least one embodiment, the fluid conduit passes into the connector hub at a port in the connector hub.

In at least one embodiment, the sterile fluid connector includes at least one sensor configured to indicate the status of fluid transfer from the sterile fluid container to the connector. For example, the sterile fluid pathway connector may further include one or more interconnects and, optionally, one or more corresponding contacts, to transmit a signal to the user. For example, the interconnect(s) may be within or at least partially proximal to a plunger seal translatable within a fluid container such that the piercing member is capable of penetrating the plunger seal and acting as a contact(s) for the interconnect(s) to transmit a signal to the user. Additionally or alternatively, the interconnect(s) or the contact(s) is within or at least partially proximal to a plunger seal translatable within a drug container and the other is within or at least partially distal to the pierceable seal to transmit a signal to the user when the plunger seal and the pierceable seal are substantially in contact. Additionally or alternatively, the interconnect(s) and contact(s) are within the sterile cavity between the connector hub and pierceable seal such that release of pneumatic and/or hydraulic pressure at the end of fluid transfer releases interconnection to transmit or cease transmission of a signal to the user. A number of known interconnects and contacts may be utilized within the embodiments of the present invention, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Another embodiment provides for an integrated fluid pathway connection and drug container having a piercing member, a connector hub, and a pierceable seal integrated at least partially within a drug container having a barrel and a plunger seal. The pierceable seal is translatable upon a substantially stationary piercing member, and the pierceable seal is configured to move from a first position, where the piercing member is positioned within a sterile cavity between the connector hub and the pierceable seal, to a second position, where the pierceable seal has been penetrated by the piercing member. The fluid container contains a fluid chamber between the pierceable seal and the plunger seal to initially retain a fluid, and the pierceable seal is configured to move from the first position to the second position by a force applied by the fluid on the pierceable seal. In at least one embodiment, the pierceable seal has a seal barrier that can be penetrated by the piercing member, and the piercing member is initially in contact with, or adjacent to, the seal barrier.

The integrated fluid pathway connection may further include a piercing member guide piece attached to the connector hub or piercing member, wherein the piercing member guide slidably engages the connector hub or piercing member to permit translation of the pierceable seal, or a portion thereof, in the direction of fluid exit from the connector. Translation of the pierceable seal in the direction of the fluid container may be prevented by retention of a portion of the pierceable seal by, for example, a housing, such as a crimped cap, mounted to the fluid container barrel that retains the connector hub, piercing member, and pierceable seal in position during operation. Such a configuration may be used to permit the fluid chamber of the fluid container to be evacuated, such as by vacuum, prior to filling with a fluid without compromising the function of the sterile fluid pathway connection.

In at least one embodiment, the connector hub has a header with a conduit port, a chamber, and a vacuum port with a channel that leads into the chamber such that the sterile cavity may be evacuated through the channel. The conduit port may have a membrane or seal that permits fluid flow out of the chamber, and may be capable of being plugged. Similarly, the vacuum port may be capable of being plugged, such as by a polymeric plug. Such configurations allow, for example, the sterile cavity to be evacuated to maintain both sterility and pressure equilibrium between the sterile cavity and the opposing side of the pierceable seal, or otherwise assist in maintaining the relative positions of the components prior to or during operation of the device by the user.

In at least one embodiment, the pierceable seal, or at least a portion thereof, is translatable upon the piercing member and the pierceable seal is further configured to move from the second position, where the pierceable seal has been penetrated by the piercing member, to a third position wherein at least one sensor indicates the status of fluid transfer from the sterile fluid container to the connector. For example, in a third position, one or more interconnects and one or more corresponding contacts are permitted to transmit a signal to the user. In one such embodiment, the interconnect(s) or the contact(s) is upon an aspect of a drive mechanism and the other is within or at least partially proximal to the plunger seal to transmit a signal to the user when the plunger seal and the pierceable seal are substantially in contact. Alternatively, the interconnect(s) or the contact(s) is within or at least partially distal to the pierceable seal and the other is proximal to the connector hub to transmit a signal to the user when the plunger seal and the pierceable seal are substantially in contact. Additionally or alternatively, the interconnect(s) and contact(s) are within the sterile cavity between the connector hub and pierceable seal such that release of pneumatic and/or hydraulic pressure at end of dose releases interconnection to transmit or cease transmission of a signal to the user. A number of known interconnects and contacts may be used with the present embodiments, which would readily be appreciated by a skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Yet another embodiment provides a fluid delivery pump with integrated sterility maintenance features comprising a housing within which an activation mechanism, an insertion mechanism, and a fluid container having a plunger seal may be mounted. The fluid container is connected at one end to a drive mechanism and at another end to a fluid pathway connection. The fluid pathway connection includes a piercing member, a connector hub, and a pierceable seal, wherein the piercing member is retained within a sterile cavity between the connector hub and the pierceable seal, and wherein the pierceable seal is configured to move from a first position to a second position in which the pierceable seal has been penetrated by the piercing member. The fluid container contains a fluid chamber between the pierceable seal and the plunger seal to initially retain a fluid, and wherein the pierceable fluid seal is configured to move from the first position to the second position by a force applied by the fluid on the pierceable seal. In at least one embodiment, the pierceable seal has a seal barrier that can be penetrated by the piercing member, and the piercing member is initially in contact with, or adjacent to, the seal barrier.

The fluid pump may further include a piercing member guide engaged with the connector hub or piercing member, wherein the piercing member guide slidably engages the connector hub or piercing member to permit translation of the pierceable seal, or a portion thereof, in the distal direction (i.e., towards the fluid conduit from where fluid exits the connector). Translation of the pierceable seal in the proximal direction may be prevented by retention of the pierceable seal, or a portion thereof, by, for example, a housing such as a crimped cap mounted to the barrel, which housing retains the connector hub, piercing member, and pierceable seal in position during operation. Such a configuration may be used to permit the drug chamber of the drug container to be evacuated, such as by vacuum, prior to filling with a fluid without compromising the function of the sterile fluid pathway connection. In at least one embodiment, the connector hub has a header with a conduit port, a chamber, and a vacuum port with a channel that leads into the chamber such that the sterile cavity may be evacuated through the channel. The conduit port may have a filter, membrane or seal to permit or restrict fluid flow out of the chamber. Similarly, the vacuum port may be capable of being plugged, such as by a polymeric plug. Such configurations may allow, for example, the sterile cavity to be evacuated to maintain sterility, the maintenance of pressure equilibrium between the sterile cavity and the opposing side of the pierceable seal, or assist in maintaining the relative positions of the components prior to or during operation of the device by a user.

In at least one embodiment, the pierceable seal is translatable upon the piercing member or an aspect of the connector hub and is further configured to move from the second position, where the pierceable seal has been penetrated by the piercing member, to a third position where one or more interconnects and one or more corresponding contacts are permitted to transmit a signal to the user. The interconnect(s) and the corresponding contact(s) are configured such that, for example: (a) the interconnect(s) or the contact(s) is positioned upon an aspect of the drive mechanism and the other is positioned within or at least partially proximal to the plunger seal, to transmit a signal to the user when the plunger seal and the pierceable seal are substantially in contact; (b) the interconnect(s) or the contact(s) is positioned within or at least partially distal to the pierceable seal and the other is positioned proximal to the connector hub, to transmit a signal to the user when the plunger seal and the pierceable seal are substantially in contact; (c) the interconnect(s) and the contact(s) are situated within the sterile cavity between the connector hub and the pierceable seal, such after the seal is pierced, continued pressure within the drug chamber causes interconnection which transmits a signal to the user, which signal is terminated once pressure inside the drug chamber drops and interconnection is lost, i.e., at end of dose. A number of known interconnects and contacts may be utilized within the embodiments of the present invention, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Additionally, the fluid pathway connections may include one or more flow restrictors. In at least one embodiment, the connector hub may at least partially function as a fluid conduit or flow restrictor. In at least one embodiment, the fluid pathway connection further includes a filter. A number of known filters can be utilized within the embodiments of the present invention, which would readily be appreciated by an ordinarily skilled artisan. For example the filter may be a permeable membrane, semi-permeable membrane, or porous membrane, which encloses the sterile cavity from the outside environment.

The novel devices of the present embodiments provide container fluid pathway connections that maintain the sterility of the fluid pathway and that are integrated into the fluid container, and fluid delivery pumps that incorporate such integrated sterile fluid pathway connections to fluid containers. Because the fluid path is disconnected until fluid delivery is desired by the operator, the sterility of the fluid pathway connection, the fluid container, the fluid, and the interior of the device as a whole is maintained. Furthermore, the novel configurations of the fluid pathway connections and fluid pumps of the present invention maintain the sterility of the fluid path through operation of the device. Because the path that the fluid travels within the device is entirely maintained in a sterile condition, only these components need be sterilized during the manufacturing process. Such components include the fluid container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the fluid pump do not need to be sterilized. This greatly improves the manufacturability of the device and reduces associated assembly costs. Accordingly, the devices of the present embodiments do not require terminal sterilization upon completion of assembly. A further benefit of the present embodiments is that the components described herein are designed to be modular such that, for example, the fluid pathway connection and other components of the device may be integrated into a housing and readily interface to function as a fluid pump.

A further embodiment provides a method of assembly of an integrated sterile fluid pathway connection and fluid container. The sterile fluid pathway connection may first be assembled and then attached, mounted, connected, or otherwise integrated into fluid container such that at least a portion of the pierceable seal is contained within the drug container. The fluid container can then be filled with a fluid for delivery to the user and plugged with a plunger seal at an end opposite the pierceable seal. The barrel can be filled with a fluid through the open proximal end prior to insertion of the plunger seal from the proximal end of the barrel. A drive mechanism can then be attached to the proximal end of the fluid container such that a component of the drive mechanism is capable of contacting the plunger seal. An insertion mechanism can be assembled and attached to the other end of the fluid conduit. This entire sub-assembly, including drive mechanism, drug container, fluid pathway connection, fluid conduit, and insertion mechanism can be sterilized, as described above, before assembly into a fluid pump. Certain components of this sub-assembly may be mounted to an assembly platform within the housing or directly to the interior of the housing, and other components may be mounted to a guide, channel, or other component or aspect for activation by the user. A method of manufacturing a fluid pump includes the step of attaching both the fluid pathway connection and fluid container, either separately or as a combined component, to an assembly platform or housing of the fluid pump. The method of manufacturing further includes attachment of the drive mechanism, fluid container, and insertion mechanism to the assembly platform or housing. The additional components of the fluid pump, as described herein, including the power and control system, the activation mechanism, and the control arm may be attached, preformed, or pre-assembled to the assembly platform or housing. In the instance in which the fluid is a drug, and the fluid pump is an ambulatory infusion device, an adhesive patch and patch liner may be attached to the housing surface of the drug pump that contacts the user during operation of the device.

A method of operating the fluid pump includes one or more of the following steps: activating, by a user, the activation mechanism; displacing a control arm to actuate an insertion mechanism; activating a drive control mechanism to push the plunger seal, connect the sterile fluid pathway connection, and drive fluid flow through the fluid pump; wherein the pushing of the plunger seal translates the fluid and thus causes a pierceable seal to deform in the direction of the fluid conduit and be pierced by a piercing member, to thereby open a fluid path from the fluid container to the fluid conduit. The drive control mechanism may be activated by actuating a power and control system. The method may further include the step of: engaging an optional on-body sensor prior to activating the activation mechanism. Furthermore, the method of operation may include translating a plunger seal within the drive control mechanism and fluid container to force fluid flow through the fluid container, the fluid pathway connection, the fluid conduit, and the insertion mechanism for delivery of the fluid to the desired target, e.g., to the body of a patient.

The novel devices of the present embodiments provide container connections which maintain the sterility of the fluid pathway and which are integrated into the fluid container, and fluid delivery pumps which incorporate such integrated sterile fluid pathway connections to fluid containers. For example, such devices are safe and easy to use, and are aesthetically and ergonomically appealing for self-administering patients.

BRIEF DESCRIPTION OF THE DRAWINGS

The following non-limiting embodiments of the invention are described herein with reference to the following drawings, wherein:

FIG. 6A is a sectional view of an embodiment of an integrated sterile fluid pathway connection, having a piercing member guide and drug container, prior to user activation; FIG. 6B shows an isometric perspective view of the piercing member guide and piercing member of the embodiment shown in FIG. 6A; and FIG. 6C is an isometric view of the piercing member guide, piercing member, and connector hub of the embodiment of FIG. 6A.

DETAILED DESCRIPTION

Figure 1A:
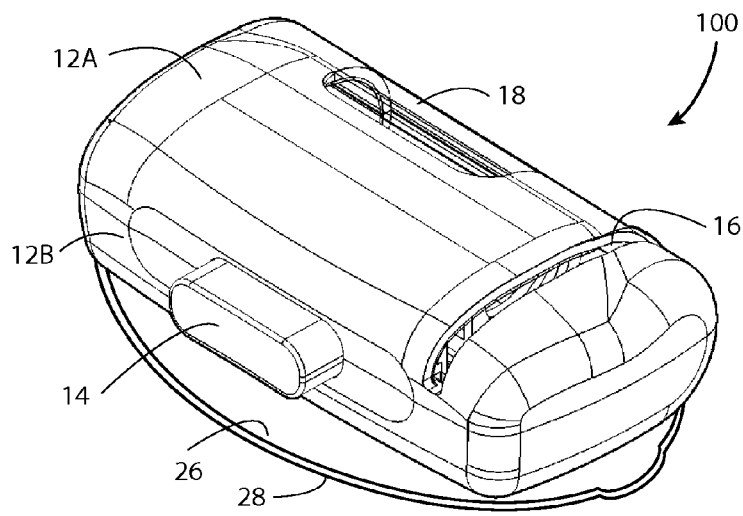
FIG. 1A is an isometric view of the surface of an ambulatory infusion pump having an integrated sterile fluid pathway connection and drug container, according to one embodiment.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

As used herein, the term "pump" is intended to include any number of drug delivery systems, such as ambulatory infusion devices, that are capable of dispensing a fluid to a user upon activation. Such drug delivery systems include, for example, injection systems, infusion pumps, bolus injectors, and the like.

As used herein to describe the integrated sterile fluid pathway connection and drug containers, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D".

As used herein, the term "glass" should be understood to include other similarly non-reactive materials suitable for use in a pharmaceutical grade application that would normally require glass, including but not limited to certain non-reactive polymers such as cyclic olefin copolymers and cyclic olefin polymers.

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, or plasticizers, etc., and that can be formed or molded under heat and pressure. As used herein, "plastic" refers to non-reactive polymers or elastomers that are approved for use in pharmaceutical applications, and in general as "plastic" neither interacts with pharmaceutical substituents, nor is degraded by contact with such substituents.

The term "elastomer," "elastomeric" or "elastomeric material" refers primarily to cross-linked thermosetting rubbery polymers that are more easily deformable than resilient plastics, are approved for use with pharmaceutical grade substances, and are not readily susceptible to leaching or gas migration under ambient temperature and pressure. It is appreciated in the art that particular elastomeric polymers are better suited for contact with pharmaceuticals than are some particular plastics, hence the elastomeric material can be a biocompatible material. As used herein, the term "elastomer," "elastomeric" or "elastomeric material" may also include other biocompatible materials, such as styrenic block copolymers, polyolefin blends, elastomeric alloys, thermoplastic polyurethanes, thermoplastic copolyesters, or thermoplastic polyamides, among other biocompatible materials which are approved for use with pharmaceutical grade substances, and are not readily susceptible to leaching or gas migration under ambient temperature and pressure.

As used herein, "needle" is intended to refer to a variety of needles including but not limited to conventional hollow needles, such as a rigid hollow steel needles, and solid core needles commonly referred to as a "trocars." For example, in one embodiment the needle is a 27 gauge solid core trocar, and in other embodiments the needle may be any size needle suitable to insert the cannula for the type of drug or drug administration intended (e.g., subcutaneous, intramuscular, intradermal, etc.).

According to various aspects and embodiments described herein, reference is made to a "biasing member", which may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

"Fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes. "Fluid" refers primarily to liquids, but can also include suspensions of solids dispersed in liquids, and gasses dissolved in or otherwise present together within liquids inside the fluid-containing portions of the pumps. "Fluid" may include agents, drugs, pharmaceuticals, and the like, but is not limited to such active agents.

References to "pharmaceutical agent," "pharmaceutically active," "pharmaceutical," "drug," "medicament," "active agent," "active drug" and the like, refer in a general sense to substances useful in the medical and scientific arts as suitable for delivery via a syringe, including, for example, drugs, biologics, diagnostic agents (e.g., dyes or contrast agents) or other substances used for therapeutic, diagnostic, or preventative (e.g., vaccines), or research purposes. Example pharmaceutical agents include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. "Inactive" substances refer to carriers, excipients, diluents, and the like, which are well-known in the art, although such substances may have beneficial function in the mixed injectable, such as, for example, adjuvants, isotonic or buffering agents. These active or inactive substances may also include substances having immediate, delayed or sustained release characteristics.

The novel embodiments presented herein provide integrated sterile fluid pathway connections and fluid containers, and fluid pumps that utilize such connections, configured to maintain the sterility of the fluid pathway before, during, and after operation of the device, and that enable active safety controls for the device. Integration of the fluid pathway connection into a portion of the fluid container helps ensure container integrity and sterility of the fluid pathway. Additionally, by integrating the sterile fluid pathway connection into a portion of the fluid container, the connection for fluid transfer can be controlled by the user (i.e., is user-activated) and enabled by the function of the drive mechanism. Accordingly, user-activation steps and the internal operation of the fluid pump can be greatly simplified by the novel integrated sterile fluid pathway connections of the present embodiments.

The novel embodiments provide container connections that maintain the sterility of the fluid pathway and are integrated into the fluid container, and fluid delivery pumps that incorporate such integrated sterile fluid pathway connections to fluid containers. The present embodiments also further integrate the sterile pathway connection into the fluid container, to reduce the necessary components or to provide easier and more efficient operation of the connection and fluid delivery pumps. The connector, the sterile fluid pathway assembly, and the infusion pump disclosed here are not limited to medical applications, but may include any application, including industrial uses, where sterile or uncontaminated fluid delivery may be desired. When the fluid is a drug, the present embodiments provide for devices that are safe and easy to use, and are aesthetically and ergonomically appealing for self-administering patients. The embodiment described herein incorporate features which make activation, operation, and lock-out of the device simple for even untrained users. One or more of the components of the present embodiments may be modular in that they can be, for example, pre-assembled as separate components and configured into position within the housing of the fluid pump device during manufacturing.

Figure 1B:
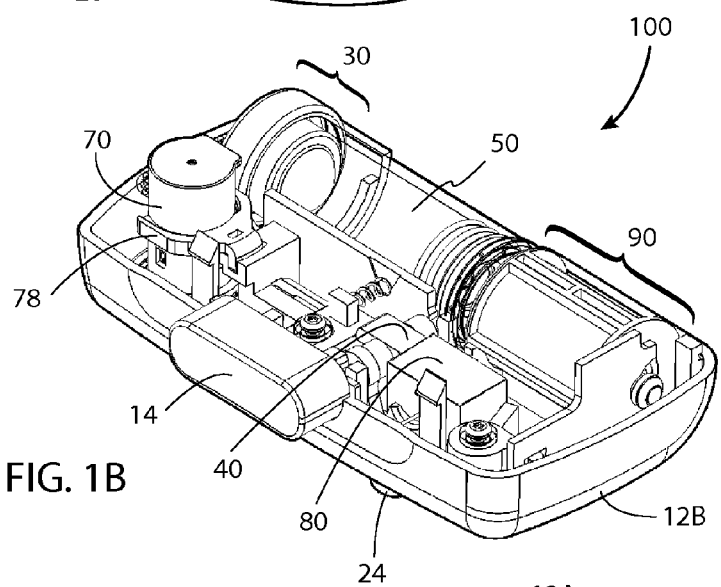
FIG. 1B is an isometric view of the interior components of the drug delivery pump shown in FIG. 1A.
Figure 1C:
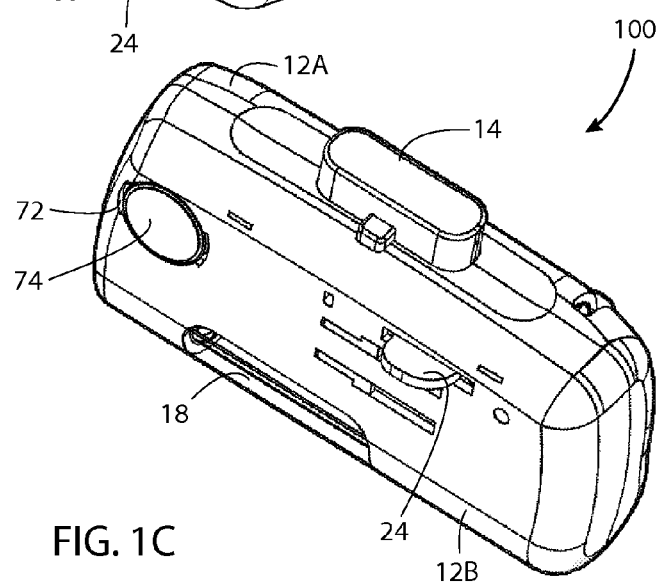
FIG. 1C is an isometric view of the other surface of the drug delivery pump shown in FIG. 1A.

Certain non-limiting embodiments of the novel fluid delivery pumps, fluid pathway connections, and their respective components are described further herein with reference to the accompanying drawings. For example, FIG. 1A to FIG. 1C show a fluid delivery device according to at least one embodiment in which fluid pump 100 includes a pump housing 12. As shown in FIG. 1B, fluid pump 100 further includes a drive mechanism 90 engaged with fluid container 50, sterile fluid pathway connection 30, insertion mechanism 70, and power and control system 80. Other sterile fluid pathway connections, drive mechanisms, insertion mechanisms and power and control systems may be used with the embodiments described herein. See, e.g., WO 2013/040032.

In the embodiment of FIG. 1, pump housing 12 may include one or more housing subcomponents that are fixedly engageable to facilitate ease in manufacturing, assembly, and operation of the device. Housing 12 includes upper housing 12A and lower housing 12B, which provide protection to the interior components of device 100 against environmental influences. Pump housing 12A, 12B include ergonomically and aesthetically designed size, shape, and related features, which facilitate easy packaging, storage, handling, and use by users who may be untrained or physically impaired. Lower housing 12B also provides a means of removably attaching the device 100 to the skin of the user, such as adhesive patch 26 and patch liner 28. The adhesive patch 26 provides an adhesive surface that can be used to adhere fluid pump 100 to the body of a user for delivery of the fluid, e.g., drug, dose. The adhesive surface of the adhesive patch 26 may initially be covered by a non-adhesive patch liner 28, which is removed from the adhesive patch 26 prior to placing fluid pump 100 in contact with the body. Removal of the patch liner 28 may further remove the sealing membrane 74 (as shown in FIG. 1C) of base 72 of insertion mechanism 70, opening the insertion mechanism to the body of the user for fluid delivery. Additionally, the external surfaces of pump housing 12A, 12B may be used to provide product labeling, safety instructions, and the like. Housing 12A, 12B may further include certain components that provide operation feedback to the user, such as status indicator 16 and window 18. Window 18 may be any translucent or transmissive surface through which the operation of the fluid pump may be viewed. Window 18 may enable the user to view the operation of fluid pump 100 or verify that fluid delivery has completed.

In at least one embodiment, fluid pump 100 includes an activation mechanism that is displaced by the user to trigger a "start command" to power and control system 80. In the embodiment of FIG. 1, the activation mechanism is start button 14, located through an aperture between upper housing 12A and lower housing 12B, and which mechanism contacts a control arm 40 of power and control system 80. In at least one embodiment, start button 14 is a push button, and in other embodiments the activation mechanism can comprise an on/off switch, a toggle, or any similar activation feature known in the art. In other embodiments, activation mechanism 14, status indicator 16, window 18, or combinations thereof, may be provided on upper housing 12A or lower housing 12B such as, for example, on a side visible to the user when the fluid pump 100 is placed on the body of a user.

In the embodiment of FIG. 1, fluid pump 100 is configured as a drug pump such that, upon activation by a user (such as by depression of the activation mechanism), the pump is initiated to: insert a fluid pathway, such as a needle or cannula, into the user; enable, connect, or open necessary fluid pathway connections between a drug container, a fluid pathway, and a sterile fluid conduit; and force drug fluid stored in the fluid container through the fluid pathway and fluid conduit for delivery into a user. One or more optional safety mechanisms may be utilized, for example, to prevent premature activation of the drug pump. For example, an optional on-body sensor 24 (shown in FIG. 1B and FIG. 1C) may be provided in at least one embodiment as a safety feature to ensure that the power and control system 80, or the activation mechanism, cannot be engaged unless the fluid pump 100 is in contact with the body of the user. In one such embodiment, on-body sensor 24 is located on the bottom of lower housing 12B where it may come in contact with the user's body. Upon displacement of on-body sensor 24 (e.g., by depression into lower housing 12B), depression of the activation mechanism is permitted. Accordingly, in at least one embodiment, on-body sensor 24 comprises a mechanical safety mechanism, such as, for example, a mechanical lock-out, that prevents unintentional triggering of fluid pump 100 by activation mechanism 14. In another embodiment, the on-body sensor may be an electro-mechanical sensor lock-out that sends a signal to the power and control system 80 to permit activation. In still other embodiments, the on-body sensor can be electrically based such as, for example, a capacitive- or impedance-based sensor that must detect tissue before permitting activation of the power and control system 80. These concepts are not mutually exclusive, and one or more combinations may be utilized within the breadth of the present invention to prevent, for example, premature activation of drug pump 100. In at least one embodiment, fluid pump 100 utilizes one or more mechanical on-body sensors. Additional integrated safety mechanisms are described herein with reference to other components of the novel fluid pumps.

One or more of the components of fluid pathway connection 30 and fluid pump 100 may be modified while remaining functionally within the breadth and scope of the present invention. For example, although the housing of fluid pump 100 is shown as two separate components (upper housing 12A and lower housing 12B) in FIG. 1, these components may be a single unified component. Adhesives or other known materials or methods may be utilized to affix one or more components of the fluid pathway connection or fluid pump to each other. For example, the upper housing and lower housing may be separate components affixed together by an adhesive, a screw fit connection, an interference fit, fusion joining, welding, ultrasonic welding, laser welding, and mechanical fastening, and the like; or the upper housing and lower housing may be a single unified component. Such standard components and functional variations would be appreciated by one having ordinary skill in the art and are, accordingly, within the breadth and scope of the present embodiments. Certain optional standard components or variations of sterile pathway connection 30 or fluid pump 100 are contemplated while remaining within the breadth and scope of the present embodiments.

The power and control system 80 may include a power source, which provides the energy for various electrical components within the fluid pump, one or more feedback mechanisms, a microcontroller, a circuit board, one or more conductive pads, and one or more interconnects. Other components commonly used in such electrical systems may also be included, as is appreciated by one having skill in the art. The microcontroller may be, for example, a microprocessor. Power and control system 80 controls several device interactions with the user and may interface with one or more other components of fluid pump 100, such as drive mechanism 90. In one embodiment, power and control system 80 interfaces with control arm 40 to identify when on-body sensor 24 or activation mechanism 14 have been activated. One or more feedback mechanisms may include, for example, tactile feedback, such as vibration; auditory tones, such as through audible alarms such as piezo alarms; or via visual indicators, such light indicators, e.g., light-emitting diodes (LEDs).

Further regarding visual feedback, power and control system 80 may interface with status indicator 16 that may be a transmissive or translucent material that permits light transfer. For example, power and control system 80 may be configured such that after the on-body sensor 24 or trigger mechanism 14 have been pressed, power and control system 80 provides a ready-to-start status signal via the status indicator 16 if device start-up checks provide no errors. During the fluid delivery process, power and control system 80 is configured to provide a dispensing status signal via status indicator 16. After fluid delivery has been completed and after the end of any additional dwell time, to ensure that substantially the entire fluid has been delivered, power and control system 80 may provide an okay-to-remove status signal via status indicator 16. This may be verified independently by the operator by viewing the drive mechanism and delivery of the fluid within the fluid container through window 18 of pump housing 12A, 12B. Additionally, power and control system 80 may be configured to provide one or more alert signals via status indicator 16, such as, for example, alerts indicative of fault or operation failure situations. Power and control system 80 may be configured to provide other, different status indicators to the user. Power and control system 80 may interface with drive mechanism 90 or integrated sterile fluid pathway connector 30 and fluid container 50 through one or more interconnects to relay such status indication, e.g., activation, fluid delivery, or completion of fluid delivery (e.g., substantial emptying of fluid container), as further described herein.

In at least one embodiment, the control interfaces between the power and control system and the other components of fluid pump 100 are not engaged or connected until activation by the user. In one embodiment, insertion mechanism 70 and drive mechanism 90 may be caused to activate directly by user operation of activation mechanism 14. This is a desirable safety feature that prevents accidental operation of the fluid pump and may also maintain the energy stored in the power source during storage, transport, and the like. In an embodiment with the optional on-body sensor, e.g., 24 in FIG. 1B, power and control system 80 powers drive mechanism 90 to deliver fluid through the integrated sterile fluid pathway connection 30 only if on-body sensor 24 remains in contact with the body of the user. The integrated sterile fluid pathway connection is connected (i.e., the fluid pathway is opened) by the pneumatic force of the drug fluid within the fluid container 50 created by activation of drive mechanism 90.

Other power and control system configurations may be utilized with the novel fluid delivery devices of the present embodiments. For example, certain activation delays may be utilized during fluid delivery. One such delay optionally included within the system configuration is a dwell time that ensures that substantially the content of the fluid container has been delivered before signaling completion to the user. Similarly, activation of the device may require a delayed depression (i.e., pushing) of the activation mechanism of the fluid pump prior to fluid pump activation. Additionally, the system may include a feature that permits the user to respond to the end-of-delivery signals and to deactivate or power-down the fluid pump. Such a feature may similarly require a delayed depression of the activation mechanism, to prevent accidental deactivation of the device. Such features provide desirable safety integration and ease-of-use parameters to the fluid pumps. An additional safety feature may be integrated into the activation mechanism to prevent partial depression and, therefore, partial activation of the fluid pumps. For example, the activation mechanism or power and control system may be configured such that the device is either completely off or completely on, to prevent partial activation. Such features are described in further detail hereinafter with regard to other aspects of the novel fluid pumps.

A number of insertion mechanisms may be used within the fluid pumps of the present embodiments. In at least one embodiment, insertion mechanism 70 includes an insertion mechanism housing having one or more lockout windows, and a base for connection to the assembly platform or pump housing (as shown in FIG. 1B and FIG. 1C). The connection of the base to the interior of the pump housing 12B may be, for example, such that the bottom of the base is permitted to pass through a hole in bottom housing 12B to permit direct contact of the base to the target, e.g., the body of a user. In such configurations, the bottom of the base 72 may include a sealing membrane 74 that is removable prior to use of the drug pump 100. The insertion mechanism may further include one or more insertion biasing members, a needle or a cannula, and a manifold. If an aspect of the insertion mechanism also requires or utilizes needle retraction, the insertion mechanism may further include a retraction biasing member. The manifold may connect to a sterile fluid conduit to permit fluid flow through the manifold, the needle or cannula, and into the target (e.g., the body of the user) during drug delivery.

When the fluid pump is configured to deliver drug to the body of a subject, the device can use a variety of needles including conventional hollow needles, e.g., rigid hollow steel needles, and solid core needles commonly referred to as a "trocars." The needle may be any size needle suitable to insert the cannula for the type of drug and drug administration intended (e.g., subcutaneous, intramuscular, intradermal, etc.). For example, the needle can be a 27 gauge solid core trocar. A sterile boot may be utilized within the needle insertion mechanism. The sterile boot is typically a collapsible sterile membrane that is in fixed engagement at a proximal end with the manifold and at a distal end with the base. In at least one embodiment, the sterile boot is maintained in fixed engagement at a distal end between base and insertion mechanism housing. The base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base 72 may be closed from non-sterile environments as well, such as by for example a sealing membrane 74 (shown in FIG. 1C).

According to at least one embodiment of the present invention, the insertion mechanism is substantially similar to that described in WO 2013033421 (PCT/US2012/053174). The insertion mechanism is initially locked into a ready-to-use stage by lockout pin(s) that are initially positioned within lockout windows of the insertion mechanism housing. In this initial configuration, insertion biasing member and retraction biasing member are each retained in their compressed, energized states. As shown in FIG. 1B, lockout pin(s) 78 can be directly displaced by user depression of the activation mechanism 14. As the user disengages any safety mechanisms (such as optional on-body sensor 24), activation mechanism 14 can be depressed to initiate the drug pump. Depression of activation mechanism 14 can directly cause translation or displacement of control arm 40, and directly or indirectly cause displacement of lockout pin(s) 78 from their initial position within corresponding locking windows of insertion mechanism 70. Displacement of lockout pin(s) 78 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle while maintaining the cannula in fluid communication with the body of the user. Accordingly, the insertion mechanism may be used to insert a needle and cannula into the user and, subsequently, retract the needle while retaining the cannula in position for drug delivery to the body of the user. In an alternative embodiment, the needle may be retained in fluid communication within the body with or without the presence of a flexible cannula. A number of insertion mechanisms may be utilized, as would readily be appreciated by one of skill in the art.

Figure 2A:
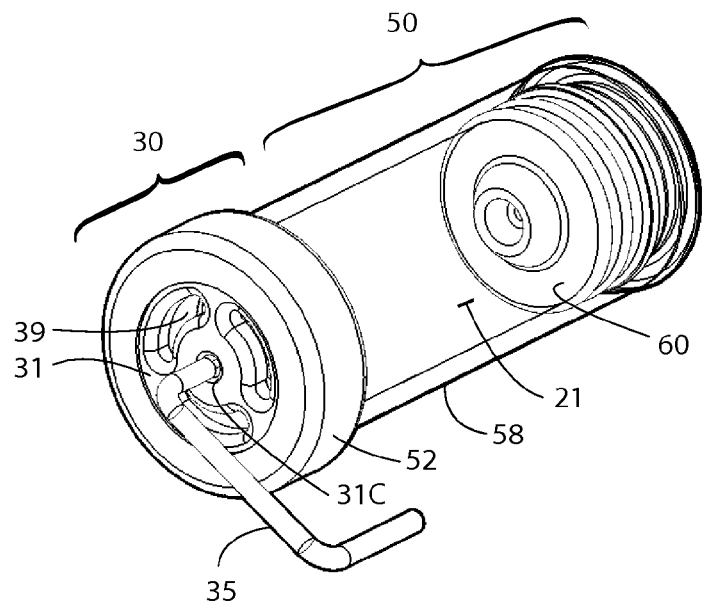
FIG. 2A is an isometric view of an integrated sterile fluid pathway connection and drug container, according to an embodiment.
Figure 2B:
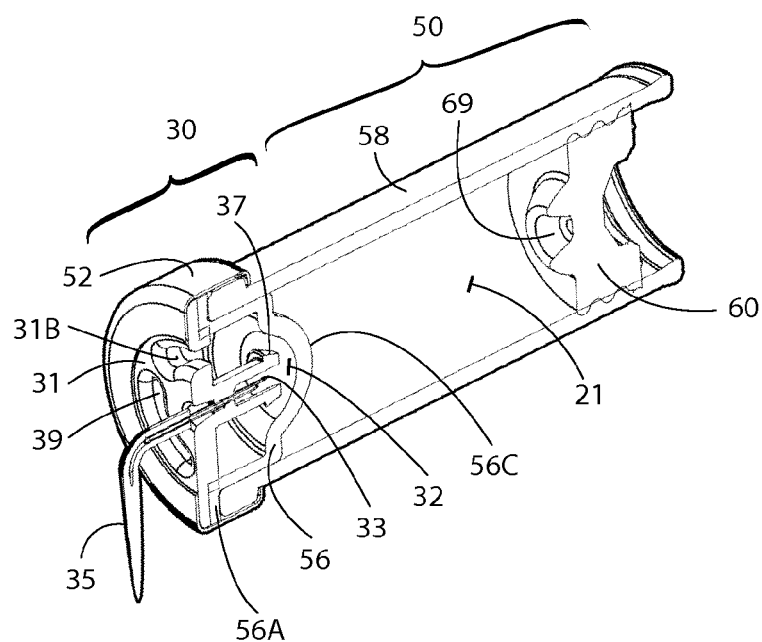
FIG. 2B is a sectional isometric view of the integrated sterile fluid pathway connection and drug container shown in FIG. 2A.

FIG. 2A and FIG. 2B show an initial configuration of an embodiment of a sterile fluid pathway connector 30 integrated with fluid container 50 having fluid chamber 21 and plunger seal 60. Fluid pathway connector 30 may be mounted, connected or otherwise attached, permanently or removably, to fluid container 50 at an end opposite plunger seal 60. As shown in the embodiment of FIG. 2A and FIG. 2B, fluid container 50 has mutable fluid chamber 21 within barrel 58, defined by the position of pierceable seal 56 and plunger seal 60. The seals described herein can be made of a number of materials, but are typically made of one or more elastomers or rubbers. Fluid chamber 21 may contain a fluid for delivery through the integrated sterile fluid pathway connector 30. In the embodiment of FIG. 2A and FIG. 2B, the fluid pathway connector 30 includes sterile fluid conduit 35, piercing member 33, connector hub 31, and pierceable seal 56. Fluid pathway connection 30 includes piercing member guide 37 engaged with connector hub 31, upon which pierceable seal 56 may interface with piercing member 33 of connector hub 31 during operation. A permeable, semi-permeable, or porous membrane, such as filter 39, may be used to allow venting of air from within the fluid pathway connector 30 during operation of the device, such as through port or vent 31B in connector hub 31. Filter 39 may be attached, mounted, bonded, over-molded, co-molded, pre-formed, or otherwise connected to enclose sterile cavity 32 between the exterior of connector hub 31 and pierceable seal 56. The term "enclose" or "enclosure" is used herein to define at least a semi-permeable or porous confined area that is capable of being sterilized, evacuated by vacuum, and vented, but is not penetrable by microorganisms, contaminants, or other undesirable environmental factors. For example, filter 39 can be over-molded at least partially within connector hub 31 to separate the sterile cavity 32 from the outside environment. In some embodiments, the filter is a membrane, e.g., a semi-permeable membrane, which allows the venting of air during the actuation of pierceable seal 56, fluid pathway connection 30, and the pump device. Filter 39 may be sterilized by methods well-known to one having skill in the art, thus the filter can maintain a sterile barrier to prevent exposure of the piercing member 33 to microorganisms, contaminants, or other undesirable environmental factors.

As shown in FIG. 2B, piercing member 33 is retained within the integrated sterile fluid pathway connection 30, at or near seal barrier 56C of pierceable seal 56. Piercing member 33 may be an aspect of fluid conduit 35 or may be a separate component from fluid conduit 35, as would readily be appreciated by one having skill in the art. Additionally, fluid pathway connector 30 may optionally include one or more gaskets, O-rings, or other sealing members, compressed to seal between barrel 58, particularly at lip 58A, connector hub 31, and housing 52. In at least one embodiment, sealing aspect 56A of the pierceable seal 56 may be configured as a seal between barrel lip 58A, connector hub 31, and housing 52. Housing 52 may be a separate component, such as a crimp cap, or may be an aspect of connector hub 31 capable of mounting to barrel 58. The housing or cap could also have screw threads configured to complement screw threads in a fluid container, or use other impermanent means for connecting the fluid container to the sterile fluid pathway connector. As shown in FIG. 2A and FIG. 2B, the sterile fluid pathway connector 30 may be attached to (i.e., integrated with) fluid container 50; which in turn can be mounted, by a number of known methods, either fixedly or removably to an assembly platform or housing of a fluid pump, such as the fluid pump as shown in FIG. 1B. The assembly platform may be a separate component from the housing, or may be a unified component of the housing such as a pre-formed mounting aspect on the interior surfaces of the housing. In such configurations, the sterility of the fluid pathway is maintained, the pathway for fluid flow is not connected until desired by the user, and user-initiated activation causes the connection of the fluid chamber and the fluid pathway connection. The fluid pathway connection may, optionally, further include one or more separate flow restrictors or one or more of piercing member 33 and fluid conduit 35 may additionally function as flow restrictors.

Figure 3A:
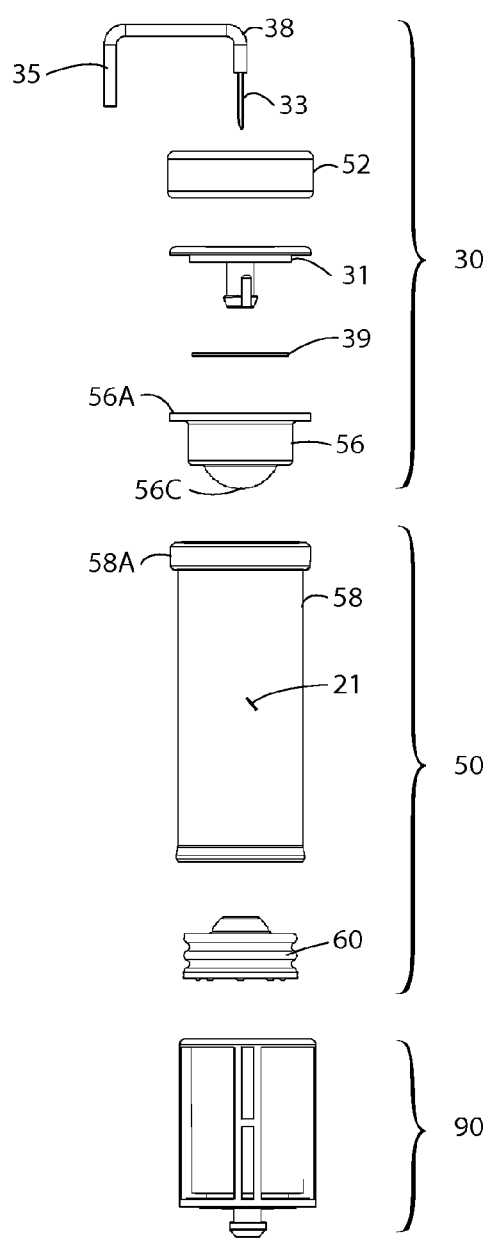
FIG. 3A is an exploded, side view of the components of an embodiment of an integrated sterile fluid pathway connection and drug container, exploded along a longitudinal axis.
Figure 3B:
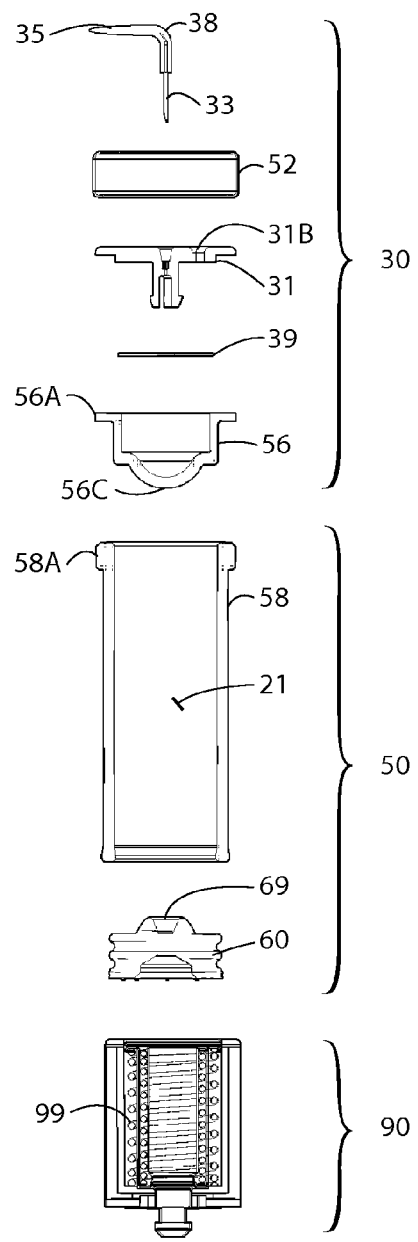
FIG. 3B is a sectional exploded view of the embodiment of FIG. 3A.

The integrated fluid connection of the present embodiments is further illustrated with reference to a drive mechanism, as shown in FIG. 3A and FIG. 3B. The embodiment comprises fluid conduit 35, engaged with piercing member 33 at engagement 38, connector hub 31 that includes vent 31B, filter 39 which is housed against connector hub 31, and pierceable seal 56, which sealing portion 56A abuts connector hub 31 and the end of barrel 58, all of which are housed in cap 52. Barrel 58 comprises mutable fluid chamber 21, and houses plunger seal 60 which is slidably disposed therein and in contact with drive mechanism 90, which includes biasing member 99. FIG. 3A is an exploded side view of components of an integrated sterile fluid pathway connector and fluid container according to at least one embodiment. FIG. 3B shows a sectional exploded view of the same embodiment. Sterile fluid pathway connector 30 may be integrated at least partially within fluid container 50 at an end opposite of plunger seal 60. An exemplary drive mechanism 90 is shown in these figures to clarify the orientation of these components. The components of the novel sterile fluid pathway connection 30 may be pre-assembled (see, e.g., FIG. 5) and subsequently attached, mounted, connected or otherwise mated, permanently or removably, with a fluid container such as fluid container 50.

A number of drive mechanisms may be utilized to force fluid from a fluid container for delivery. In one such embodiment, the drive mechanism 90 may be substantially similar to that described in WO 2013/033467 (PCT/US2012/053241). The components of the drive mechanism upon activation, may be used to drive axial translation in the distal direction (i.e., toward housing 52 of FIG. 2) of the plunger seal of the fluid container. Optionally, the drive mechanism may include one or more compliance features that enable additional axial translation of the plunger seal to ensure, for example, that substantially the entire drug dose has been delivered to the user and that the feedback contact mechanisms have connected or interconnected. Furthermore, the drive mechanism may include one or more safety mechanisms, such as premature activation prevention mechanisms, to enhance the safety and usability of the mechanism and the device.

In a particular embodiment, drive mechanism 90 employs one or more compression springs 99 as biasing member(s), as shown in FIG. 3B. Upon activation of the fluid pump by the user, the power and control system is actuated to directly or indirectly release the compression spring(s) from an energized state. Upon release, the compression spring(s) may bear against and act upon the plunger seal 60 to force the fluid out of the mutable fluid chamber 21 of drug container 50 as further described with reference to FIG. 4.

Figure 4A:
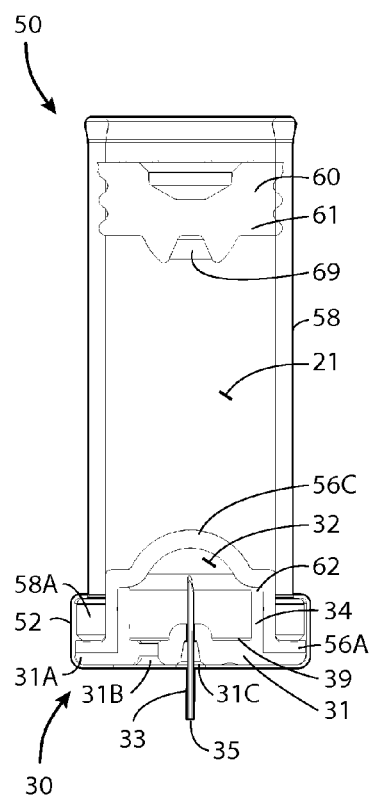
FIG. 4A is a sectional view of an integrated sterile fluid pathway connection and drug container, as shown in FIG. 2A, prior to user activation.
Figure 4B:
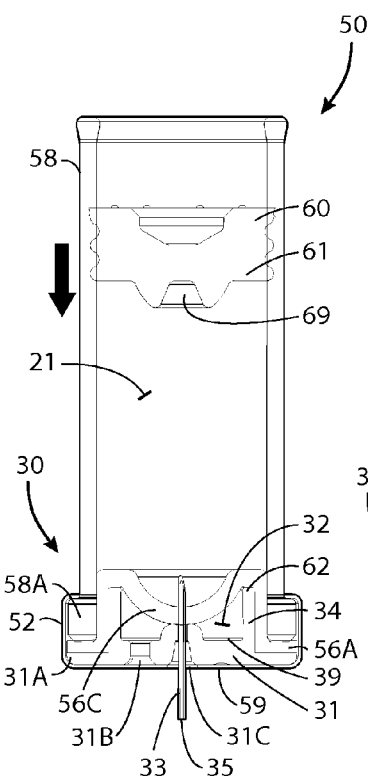
FIG. 4B is a sectional view of the embodiment with the fluid pathway connected.
Figure 4C:
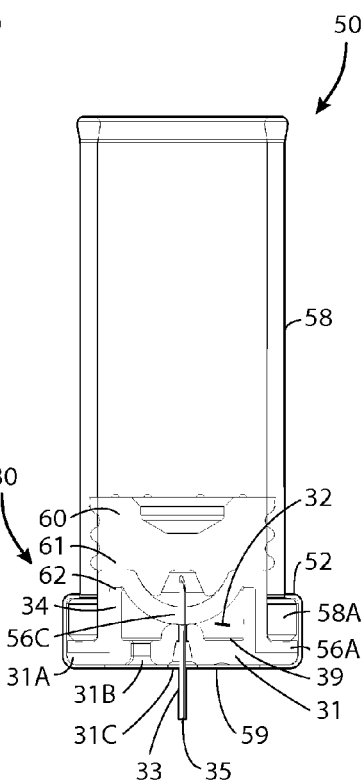
FIG. 4C is a sectional view of the embodiment at the end of drug delivery.

FIG. 4A to FIG. 4C illustrate the features of an embodiment before use, upon piercing of the pierceable seal, and upon completion of fluid delivery. More specifically, in the configuration shown in FIG. 4A, piercing member 33 is maintained within sterile cavity 32 with a first end (a proximal end) adjacent to, or contacting, pierceable seal 56 of fluid pathway connector 30. The sterility of cavity 32 and piercing member 33 is maintained, for example, by filter 39 disposed between sterile cavity 32 and the outside environment. In at least one embodiment, as shown in FIG. 4, filter 39 is connected to, engaged with, or part of connector hub 31, and encloses sterile cavity 32 from the outside environment. Sterile cavity 32 can be vented via vent or port 31B within hub connection 31. Accordingly, fluid pathway connector 30, in at least one embodiment, is mounted to and integrated with fluid container 50, for example by housing (cap) 52 engaged with lip 58A of barrel 58. The piercing member may be a number of cannulas or conduits, such as rigid needles, and may be comprised of a number of materials, such as steel. In at least one embodiment, piercing member 33 is a rigid steel needle. Pierceable seal 56 may have sealing aspect 56A that permits pierceable seal 56 to be mounted directly to or otherwise held in position between barrel 58, connector hub 31, and cap 52. Connector hub 31 includes an internal seal mount 34 that further stabilizes the position of more stationary aspects of pierceable membrane 56. At least a portion of pierceable seal 56, such as seal barrier 56C, is translatable upon connector hub 31, as described herein, to rupture against piercing member 33 and enable the fluid pathway connection to sterile fluid conduit 35. Advantageously, such an arrangement permits pierceable seal 56 to translate towards cap 52 but not towards the plunger seal 60. This is a desirable feature that permits the mutable fluid chamber 21 of the fluid container 50 to be evacuated, such as by vacuum, prior to filling with a fluid without compromising the function of sterile fluid pathway connector 30.

In an initial position the proximal end of piercing member 33 may reside adjacent to, or in contact with, seal barrier 56C of pierceable seal 56 to, for example, minimize the distance of translation of the seal barrier 56C to become pierced and open fluid container 50 to fluid pathway connector 30. In a particular embodiment, proximal end of the piercing member 33 may reside at least partially within seal barrier 56C of pierceable seal 56, yet not fully passing there-through, until activation of the device by a user.

As shown in FIG. 4B, once the pump device is activated and the drive mechanism pushes plunger seal 60, plunger seal 60 asserts a force on fluid chamber 21, and pneumatic and/or hydraulic pressure builds by compression of the fluid in chamber 21. As pneumatic and/or hydraulic pressure builds within fluid chamber 21, the force is relayed to pierceable seal 56, causing barrier seal 56C to transform. This transformation may include a shift, inversion, translation, flexion, deformation, pop, snap, or any other functionally equivalent change, such that a portion of pierceable seal 56, such as seal barrier 56C, impinges against the substantially fixed position of piercing member 33 and causes piercing member 33 to pierce pierceable seal 56 at seal barrier 56C, as shown in FIG. 4B, thereby opening or otherwise connecting the fluid pathway between mutable fluid chamber 21, piercing member 33, and fluid conduit 35.

Accordingly, integrated sterile fluid pathway connector 30 is connected (i.e., the fluid pathway is opened) by the pneumatic and/or hydraulic force of the fluid within the fluid chamber 21 created by activation of the drive mechanism. Once integrated sterile fluid pathway connection 30 is connected or opened, fluid is permitted to flow from the fluid container 50, through integrated sterile fluid pathway connection 30 and sterile fluid conduit 35. In aspects in which the fluid pump is an ambulatory drug infusion pump, fluid drug then flows through the insertion mechanism and into the body of the user for drug delivery. In at least one embodiment, a number of flow restrictors may be optionally utilized to modify the flow of fluid within the fluid pathway connection. In at least one embodiment, the fluid flows through only a manifold and a cannula or needle of the insertion mechanism, thereby maintaining the sterility of the fluid pathway before and during fluid delivery.

Additionally or alternatively, plunger seal 60 or the pierceable seal 56 may have some compressibility permitting a compliance push of fluid from drug container 50. Additionally, the drive mechanism, plunger seal 60, connector hub 31, pierceable seal 56, or a combination thereof, may include one or more sensors or status indication mechanisms, such as interconnects and contacts, to measure and communicate the status of drug delivery drive before, during, and after operation of the device to deliver fluid.

FIG. 4C shows the components of fluid container 50 and sterile fluid pathway connector 30 after substantially all of the fluid has been pushed out of the fluid container 50. In particular, plunger seal 60 is in the most-distal position in barrel 58. In the embodiment of FIG. 4C, the connector hub-side (e.g., distal end) of plunger seal 60 is configured with an optional protrusion and cavity aspect 69, which structure minimizes residual volume left in fluid chamber 21, now collapsed. Alternatively, plunger seal may be a flat-faced plunger seal (e.g., plunger seal 160 in FIG. 6A and FIG. 7), or may have any number of other configurations as would be readily appreciated by one having skill in the art. In the embodiment shown in FIG. 4, plunger seal 60 further comprises interconnect/contact 61; and connector hub 31 further comprises interconnect/contact 62. At end-of-delivery, interconnect/contact 61 of plunger seal 60 and interconnect/contact 62 of connector hub 31 interconnect and transduce a signal that may be perceived by a user. As described herein, numerous sensors and signal transducing means can be incorporated or adapted for use in the present embodiments.

Because of the novel design of the fluid pathway connector of the present embodiments and their integration at least partially within fluid containers, sterility of the fluid pathway is maintained throughout transport, storage, and operation of the device; user-activation of the device is simplified; and the fluid pathway is only connected when desired by the user. The sterility of the fluid pathway connection is initially maintained by performing the connection within a sterile cavity 32 between connector hub 31, pierceable seal 56, and piercing member guide 37. In at least one embodiment, the sterility of cavity 32 is maintained by filter 39 that abuts, is engaged with or part of, connector hub 31. Filter 39 may be, for example, a semi-permeable membrane that allows the venting of air through vent 31B of connector hub 31 during the actuation and translation of pierceable seal 56. Filter 39 may be sterilized by typical sterilization methods, which would readily be appreciated by one having skill in the art, and may be used to maintain a sterile barrier that prevents exposing piercing member 33 to microorganisms, contaminants, or other undesirable environmental factors. For example, upon substantially simultaneous activation of the insertion mechanism, the fluid pathway between mutable fluid chamber 21 and insertion mechanism is complete to permit drug delivery into the body of the user. Because fluid pathway connector 30 is not in fluid connection or communication with fluid chamber 21 until activation of the fluid pump and drive mechanism, fluid flow from the fluid container 50 is prevented until desired by the user. This provides an important safety feature to the user and also maintains the container integrity of the fluid container and sterility of the fluid pathway The drive mechanism that translates the plunger seal 60 may contain one or more drive biasing members (e.g., as shown in FIG. 3B). The components of the drive mechanism function to force a fluid from the mutable fluid chamber 21 through pierceable seal 56 and through the piercing member 33 or sterile fluid conduit 35, for delivery through fluid pathway connector 30. Further regarding the drive mechanism, a number of drive mechanisms may be utilized to force fluid from a drug container for delivery into the body of a user. In one such embodiment, the drive mechanism 90 may be substantially similar to that described in WO 2013/033467 (PCT/US2012/053241). The components of the drive mechanism, upon activation, drive axial translation in the distal direction of the plunger seal of the drug container. Optionally, drive mechanism may include one or more compliance features which enable additional axial translation of the plunger seal to, for example, ensure that substantially the entire fluid dose has been delivered to the user and make sure that the feedback contact mechanisms have connected. Furthermore, the drive mechanism may include one or more safety mechanisms, such as premature activation prevention mechanisms, to enhance the safety and usability of the mechanism and the device.

Figure 5A:
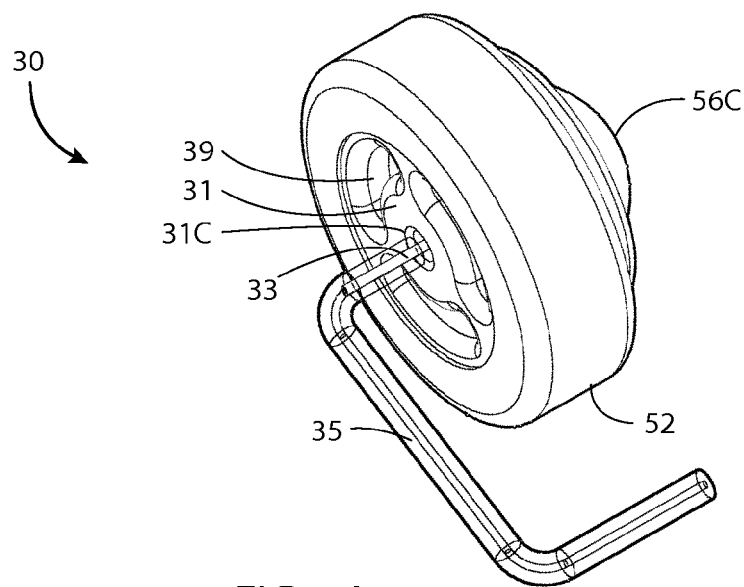
FIG. 5A is an isometric perspective view, of the integrated sterile fluid pathway connection according to an embodiment of the present invention.
Figure 5B:
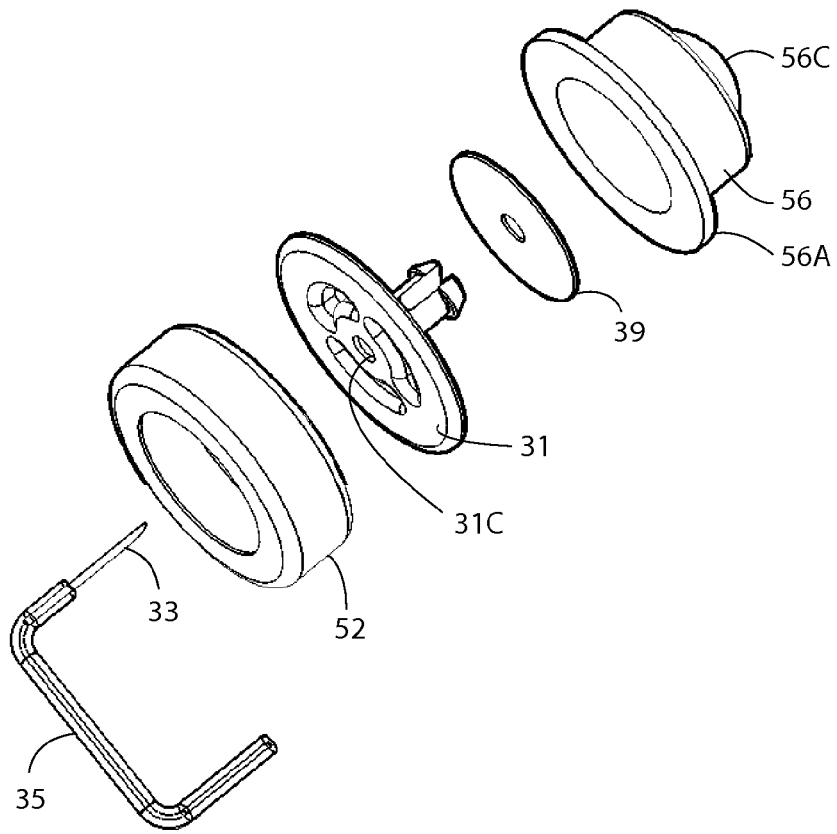
FIG. 5B is an exploded, perspective view of the components of the integrated sterile fluid pathway connection shown in FIG. 5A.

At least one embodiment provides for a modular fluid pathway connection. FIG. 5A and FIG. 5B detail an embodiment of a modular fluid pathway connector that comprises connector hub 31, which abuts filter 39 and pierceable seal 56 at sealing member 56A. Connector hub 31, filter 39 and pierceable seal 56 are housed within cap 52, as shown in FIG. 5A. Connector hub 31 further comprises header 31C, which forms a junction for fluid conduit 35 and piercing member 33. As shown in FIG. 5A and FIG. 5B, fluid conduit 35 may be connected directly to piercing member 33. Alternatively, as shown in FIG. 6A fluid conduit 235 may be connected via conduit port 238. Nevertheless, a modular fluid pathway connection can be adapted for use with a number of alternative barrel and drive configurations, and used within a variety of ambulatory infusion devices. The components of the novel sterile fluid pathway connector 30 may be pre-assembled, to appear as exemplified in FIG. 5A, and subsequently attached, mounted, connected, or otherwise mated with a fluid container such as fluid container 50. Alternatively, the components of sterile fluid pathway connector 30 may be assembled directly into drug container 50. As would be readily appreciated by one skilled in the art, a number of glues or adhesives, or other connection methods such as snap-fit, interference fit, screw fit, fusion joining, welding, ultrasonic welding, laser welding, and mechanical fastening, and the like, can be used to engage one or more of the components described herein in permanent or impermanent connection as desired for a particular use. For example, glue can be used between distal end of barrel 58, sealing member 56A, or connector hub 31A. Additionally or alternatively, the components of the sterile fluid pathway connector 30 may be mounted to barrel 58 and held in place crimping cap 52 to distal aspect of barrel 58, such as to a flanged aspect or lip of barrel 58A.

In at least one embodiment, as shown in FIG. 6A to FIG. 6C, piercing member guide 237 may be utilized to guide pierceable seal 56 and to slidably engage the connector hub 231. Additionally or alternatively, piercing member guide 237 may be utilized to ensure that piercing member 233 remains substantially centered on the axis so as to pierce pierceable seal 56 at the desired portion of seal barrier 56C. The embodiment of FIG. 6A shows fluid container comprising barrel 58 and forming mutable fluid chamber 21 between plunger seal 260 and pierceable seal 56. As shown in FIG. 6A, plunger seal 260 is a flat plunger seal, but a variety of plunger seal shapes can be adapted for use with the fluid connection and infusion pumps of the present embodiments. The embodiment of FIG. 6A further comprises filter 39, which abuts connector hub 231 and is used to maintain sterility of sterile chamber 32 between connector hub 231 and pierceable seal 56. Connector hub 231 also includes seal mount 234 that abuts pierceable seal 56; and flange 231A that abuts seal member 56A of seal 56, and that, in turn, abuts the distal lip 58A of barrel 58. The meeting surfaces of connector hub 231A, sealing member 56A and barrel lip 58A are positioned in place and secured within the rims of cap 52. Connector hub 231 also houses piercing member 233, which connects to fluid conduit 235. Connector hub 231 also has vacuum port 231B, a filtered channel that leads into sterile chamber 32. Connector hub 231 is also configured with conduit port 231D, which provides exit from sterile fluid connector 230 to the rest of the infusion device (e.g., injection means), such as via sterile fluid conduit 35 (not shown). Conduit port 231D and vacuum port 231B may contain a membrane or seals, such as one-way seals, which permit fluid flow out of chamber 32 through the respective ports but do not permit fluid flow into the chamber 32 through these ports. Additionally, or alternatively, conduit port 231D and vacuum port 231B may be plugged at certain points of assembly or operation. For example, vacuum port 231B may be used to evacuate sterile cavity 32 during manufacturing, assembly, or at any point prior to operation of the device; and then vacuum port 231B can be plugged after the evacuation has been completed.

Further regarding piercing member guide 237, this component may be slidably attached to connector hub 231. A number of means known in the art may be used to facilitate this slidable attachment such as, for example, engagement between a connector prong 237D and leg 237A of piercing member guide 237 with complementary cavity 236 in connector hub 231. These components are more clearly visible in FIG. 6A and FIG. 6B. FIG. 6B shows the orientation of piercing member 233 within piercing member guide 237, which emerges from piercing member guide 237 at header 237C; and FIG. 6C shows the orientation of piercing member 33 and piercing member guide 237 within connector hub 231. Such an arrangement permits the pierceable seal 56 and piercing member guide 237 to translate towards housing 52 together, at least for a portion of the translation of seal barrier 56C. Additionally, pierceable seal 56 may be removably attached to piercing member guide 237 by a number of means known in the art such as, for example, removable snap-fit engagement or it may be configured to enable contact between the components to guide the translation of the seal barrier 56C upon the piercing member 233. When a piercing member guide is used, such as piercing member guide 237 in FIG. 6A, the piercing member guide may translate with pierceable seal 56, for at least a portion of the translation, to ensure that the seal barrier 56C contacts and is pierced by the piercing member 233. Once the fluid pathway is opened or connected, translation of plunger seal 160 in the distal direction by the drive mechanism causes fluid within drug chamber 21 to be forced through the sterile fluid connector. In some embodiments, a needle insertion mechanism, as described herein, may be connected at the other end of the fluid conduit 35 to insert a needle into the body of the user to facilitate fluid transfer to the user.

The embodiment shown in FIG. 6A also comprises plunger seal 260, which may be used as a part of the status indication mechanism along with piercing member guide 237. More specifically, in this embodiment plunger seal 260 includes interconnect/contact 261 and the corresponding interconnect/contact 262 is located on piercing member guide 237. When plunger seal 260 and piercing member guide 237 reach proximity at end-of-delivery (e.g., as in FIG. 4C), interconnect/contact 261 and interconnect/contact 261 interconnect and transduce a perceptible signal to the user.

The novel embodiments presented herein provide integrated sterile fluid pathway connections and fluid containers, and fluid pumps that utilize such connections, that are configured to maintain the sterility of the fluid pathway before, during, and after operation of the device, and that enable active safety controls for the device. Integration of the fluid pathway connector into a portion of the fluid container helps ensure container integrity and sterility of the fluid pathway. Additionally, by integrating the sterile fluid pathway connector into a portion of the fluid container, the connection for fluid transfer can be controlled by the user (i.e., user-activated) and enabled by the function of the drive mechanism. Accordingly, user-activation steps and the internal operation of the fluid pump can be greatly simplified by the novel integrated sterile fluid pathway connections of the present embodiments.

Figure 7:
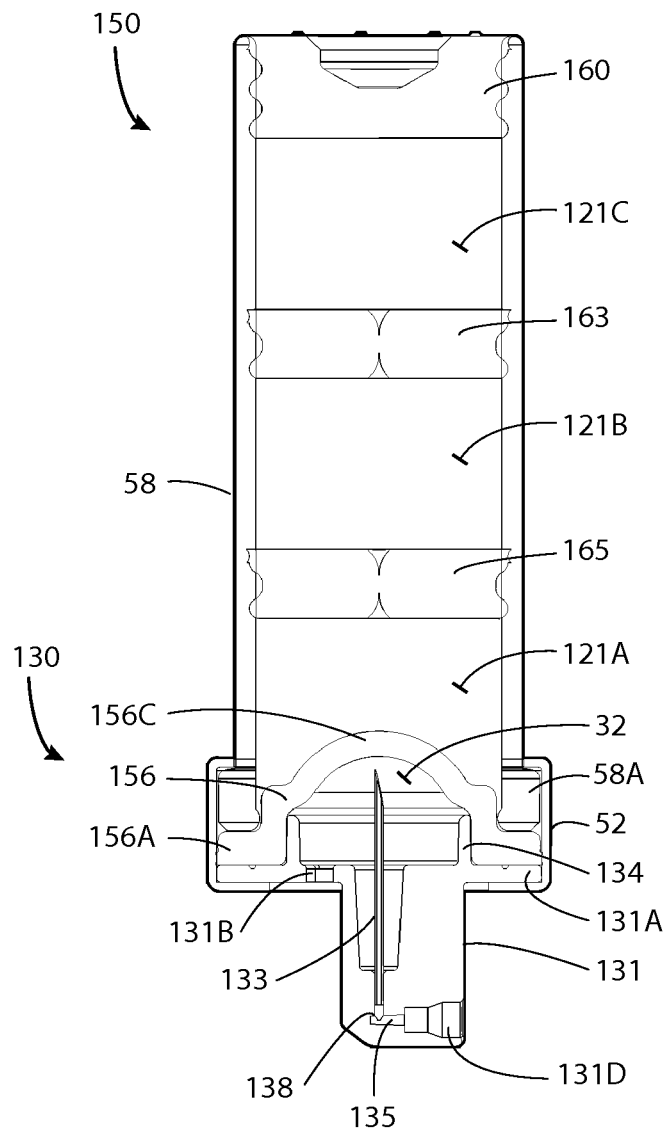
FIG. 7 is a cross-sectional view of an integrated sterile fluid pathway connection and drug container according to an embodiment prior to user activation, in which the drug container comprises more than one drug chamber, each drug chamber separated from the next by a pierceable membrane.

In another embodiment, the fluid container comprises at least two mutable internal compartments, wherein each compartment-compartment interface comprises a distinct pierceable seal capable of being disrupted by the piercing member of the sterile fluid pathway connector to create a sterile fluid communication between the sterile fluid pathway and that compartment of the sterile fluid container. As shown in FIG. 7, container 50 may utilize one or more seals in addition to plunger seal 160 and pierceable seal 156. This may be applicable, for example, when multiple fluid substances are desired to be delivered by the container and the infusion pump device. FIG. 7 shows one such embodiment that utilizes two additional seals, 163 and 165, to create compartments or chambers 121A, 121B and 121C, within which one or more fluid substances may be stored for delivery. The embodiment of FIG. 7, pierceable seal 156 includes seal barrier 156C and base 156A, which base 156A abuts barrel lip 58A on its distal side and connector hub 131A on its proximal side, which abutments are held within housing 52. Connector hub 151 further includes vacuum port 131B, with a channel that leads into sterile chamber 32. Connector hub 131 is also configured with conduit port 131D, which provides exit from sterile fluid connector 130 to the rest of the infusion device (e.g., an injection mechanism). Conduit port 131D and vacuum port 131B may each contain a membrane, filter or seals, such as one-way seals, which permit fluid flow out of chamber 32 through the respective ports but do not permit fluid flow into the chamber 32 through said ports. Additionally, or alternatively, conduit port 131D and vacuum port 131B may be plugged at certain points of assembly or operation. For example, vacuum port 131B may be used to evacuate sterile cavity 32 during manufacturing, assembly, or at any point prior to operation of the device; and then vacuum port 131B can be plugged after the evacuation has been completed.

Upon activation of the fluid pump, pressure at interface 168 of plunger seal 160 causes distal translation of plunger seal 160 towards housing 52. The pneumatic and/or hydraulic pressure within the fluid substance(s) held in drug chambers 121A, 121B and 121C relays the force to, and causes distal translation of, chamber seal 163, chamber seal 165, and pierceable seal 156, causing seal barrier 156C to translate towards housing 52 and become pierced by piercing member 133. This causes the sterile fluid pathway connection to be made or opened, as described herein. Upon further translation of plunger seal 160, the fluid substance held in mutable drug chamber 121A is dispensed through conduit 135. Upon further translation of the fluids and seals, seal 165 may be then be pierced by piercing member 133, thereby permitting the fluid substance in mutable fluid chamber 121B to be dispensed from the fluid pathway connector. If further compartments or chambers are desired, more seals and chambers (such as seal 163 and mutable chamber 121C) may be configured, and subsequently engaged in the same manner until plunger seal 160 has been fully translated towards housing 52. This configuration may offer advantages over single-compartment fluid containers. For example, a diluent may be stored in mutable fluid chamber 121A and a therapeutic drug may be stored in mutable fluid chamber 121B, such that the sterile fluid pathway is first purged by the diluent prior to delivery of the drug therapy to the patient. When drug combinations are desired for delivery, multiple therapeutic agents may be stored and delivered using the configuration provided by this embodiment. Any number of seals and drug chambers may be utilized in such a configuration provided that the piercing member 133, the drive mechanism, and other components of the embodiments are configured appropriately for such delivery.

The novel integrated sterile fluid pathway connectors of the present invention may additionally incorporate status indication into the fluid delivery mechanisms. Such status indication features may be incorporated into the drive mechanism 90, as described in WO 2013033467. Additionally or alternatively, status indication features may be incorporated into the components of the sterile fluid pathway connectors. In one embodiment, one or more interconnects are contained within, or proximal of, the plunger seal. At the end of fluid delivery, the piercing member may be utilized to contact the, or as a contact for, interconnect to open, close, or otherwise create a signal to the power and control system to provide feedback to the user. In another embodiment, one of either interconnects/contacts are contained within, or proximal of the plunger seal, while the other is contained within or distal of the pierceable seal, such as in or on a seal mount or guide piece. At the end of fluid delivery, interconnects and corresponding contacts are close enough to permit a signal to be sent to the power and control system to provide feedback to the user.

In another embodiment, the surface of the connector hub sequestered in sterile chamber 32 may incorporate, or itself be utilized as, a contact or interconnect for the status indication mechanism. For example, an end-of-delivery signal can be provided using a leaf/flex arm or spring style switch mechanism contained within sterile compartment 32, engaged with the surface of the connector hub and connected through the hub to the appropriate electronics. In this arrangement, in the unpressurized state (before device activation), the switch rests in the open position, and there is no contact/interconnect or signal transduced. When the device is activated, i.e., when the drive engages the plunger seal within the drug container, pneumatic and/or hydraulic pressure causes the pierceable seal to translate into the piecing member, thus disrupting the pierceable seal and allowing fluid to flow through the sterile fluid connector. Pneumatic and/or hydraulic pressure further causes the septum of the pierceable seal to press against the switch mechanism until it interconnects with its complementary contacts, which closes the circuit and allows a signal to transduce to the user, indicating that drug delivery has started. At end-of-delivery, the pneumatic and/or hydraulic pressure within the sterile chamber is released and the switch re-opens, breaking the circuit and providing an end-of-delivery signal to the user.

Figure 8A:
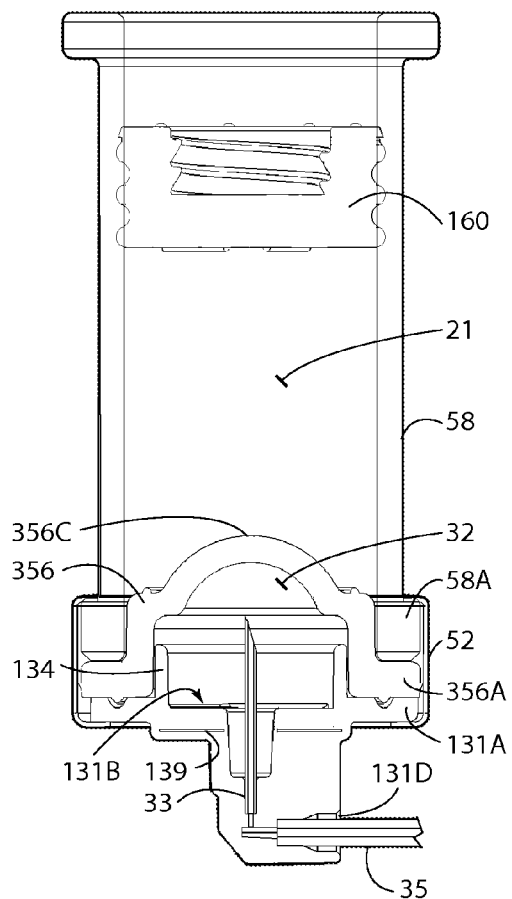
FIG. 8A to FIG. 8E are sectional views of an embodiment of a sterile fluid connector in which the pierceable seal is configured to maintain different positions within the connector in response to pneumatic and/or hydraulic pressure.
Figure 8B:
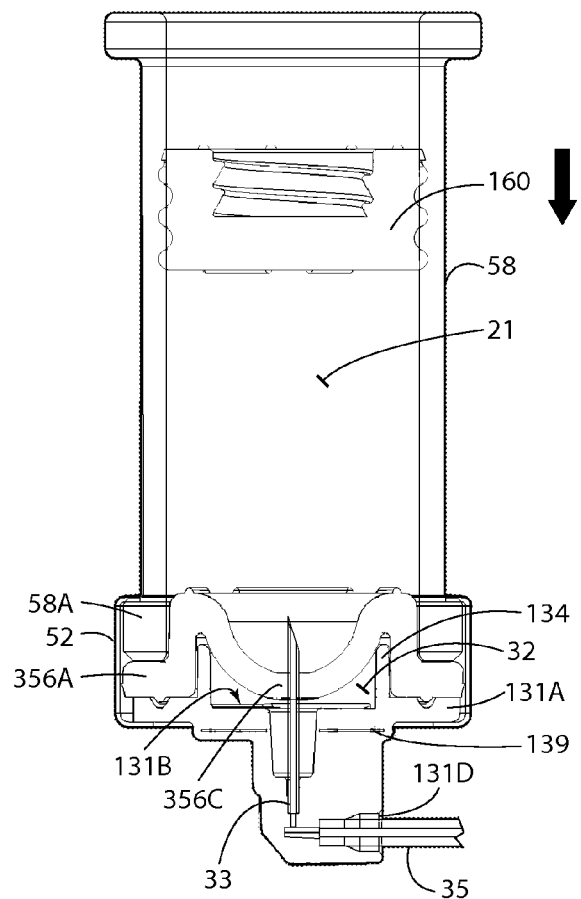
Figure 8C:
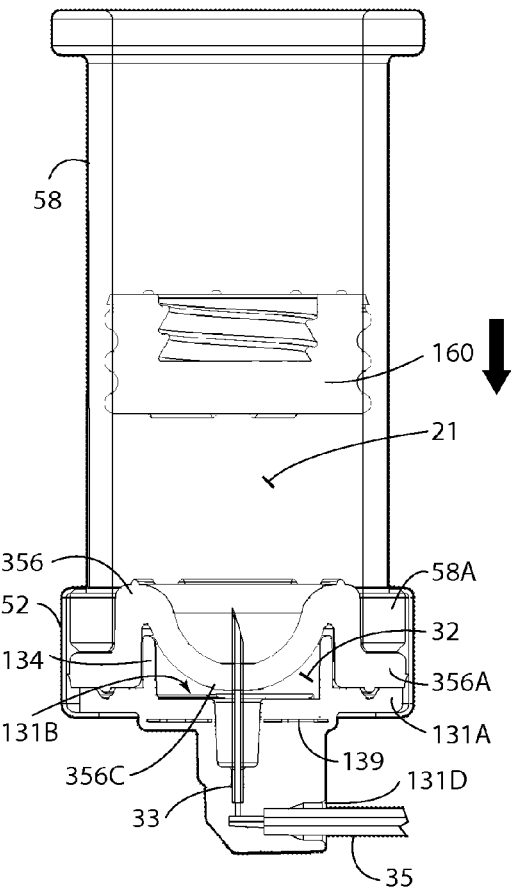
Figure 8D:
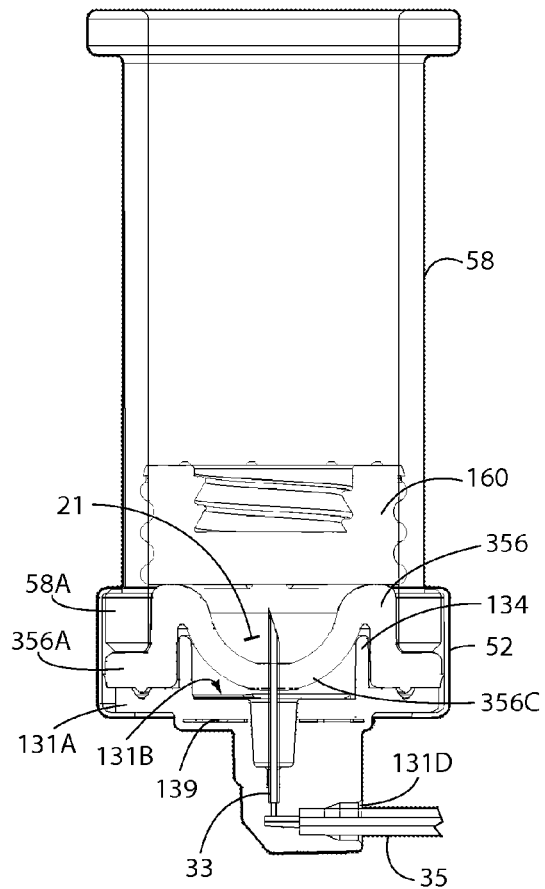
Figure 8E:
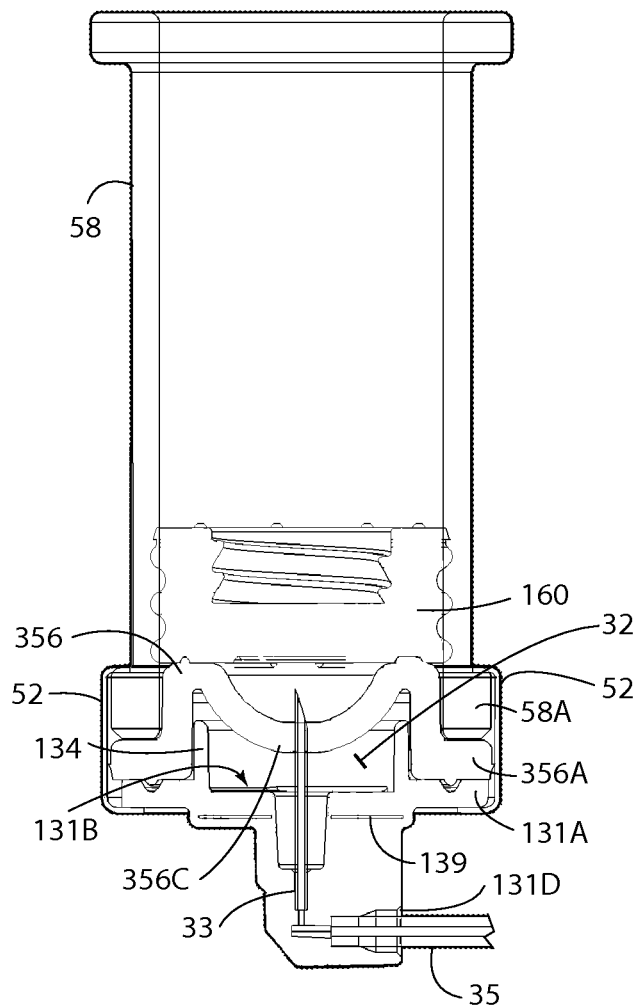

Such a configuration, in which the surface of the connector hub sequestered in the sterile chamber of the sterile fluid pathway connector may incorporate, or itself be utilized as, a contact or interconnect for the status indication mechanism, may be facilitated by a configuration of the pierceable seal. For example, as shown in FIG. 8A to FIG. 8E, fluid chamber 58 comprises plunger seal 160, configured to engage a drive mechanism that forces plunger seal 160 towards sterile fluid connector 130. In the initial position (i.e., before the drive is engaged), pierceable seal 356 maintains sterile chamber 32 within the space defined by pierceable seal 356 and connector hub 131, particularly as partially maintained by seal mount 134, as shown in FIG. 8A. Connector hub 131 further includes piercing member 33, and vacuum port or vent 131B in which sterility of chamber 32 is maintained by filter 39. Connector hub base 131A, sealing member 356A of pierceable member 356, and barrel lip 58A are all secured in housing 52, which housing can be a cap such as a crimp cap. Connector hub 131 also includes exit port 131D, which provides an exit passage for fluid conduit 35 from the sterile fluid pathway connector. Once a pump drive is activated and plunger seal 160 is forced toward piercing member 33, pneumatic and/or hydraulic pressure within mutable fluid chamber 21 forces seal barrier 356C of pierceable seal 356 into piercing member 33, which pierces seal barrier 356C and opens the sterile fluid pathway. Continued pneumatic and/or hydraulic pressure within mutable chamber 21 forces at least a portion of pierceable seal 356 to contact at least a portion of connector hub 131 within sterile chamber 32, as shown in FIG. 8B. This continued pneumatic and/or hydraulic pressure, as long as the drive is activated and fluid remains in mutable chamber 21, maintains the contact between seal 356 and connector hub 131, as shown in FIGS. 8C and 8D. When fluid has been pumped out of mutable fluid chamber 21, such that this chamber essentially no longer exists, pneumatic and/or hydraulic pressure against seal 356 is released, and seal 356 returns to a non-pressurized state within chamber 32, in which there is no longer contact between seal 356 and hub 131, as shown in FIG. 8E.

Figure 9A:
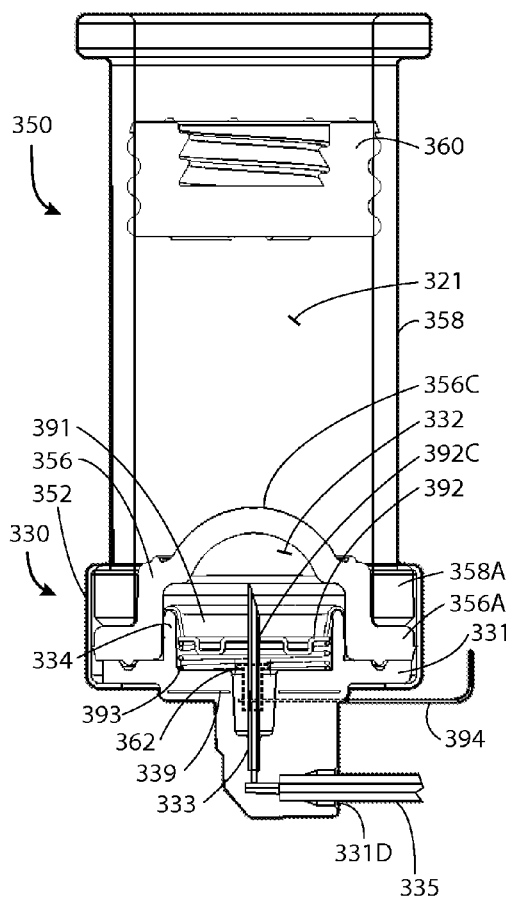
FIG. 9A to FIG. 9H are sectional and isometric sectional views of an embodiment of a sterile fluid connector in which the pierceable seal, in response to pneumatic and/or hydraulic pressure, engages or disengages a sensor mechanism that is capable of transmitting a signal indicating the status of fluid transfer from the sterile fluid container to the connector.
Figure 9B:
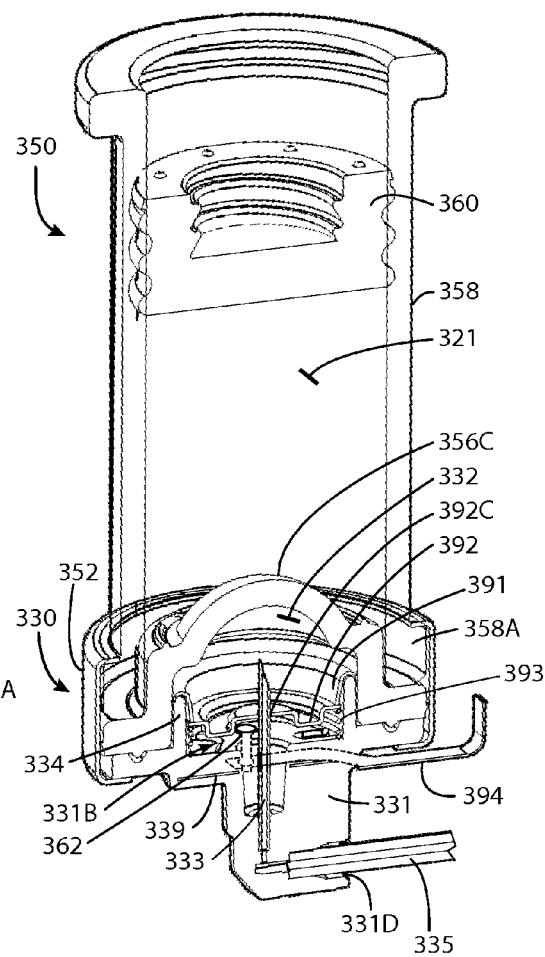

This aspect of the embodiments is advantageous for a number of devices and configurations useful to provide the sterile fluid pathway connector with at least one sensor configured to indicate the status of fluid transfer from the sterile fluid container to the connector. An example of such a sensor is a "switch" mechanism contained within the sterile chamber in the sterile fluid connector. For example, in the embodiment shown in FIG. 9 to FIG. 9H, fluid container 350 includes barrel 358, which houses fluid chamber 321 and plunger seal 360, configured to engage a drive mechanism that forces plunger seal 360 and fluid in mutable fluid chamber 321 toward sterile fluid connector 330. Pierceable seal 356 maintains sterile chamber 332 within the space defined by pierceable seal 356 and connector hub 331, as shown in FIG. 9A and FIG. 9B, in which the fluid pathway is "closed." Connector 330 further includes connector hub 331, which further vacuum port 331B, in which sterility of chamber 332 is maintained by filter 339; exit port 331D, which provides an exit passage for fluid conduit 335 from sterile fluid pathway connector 330; and engages piercing member 333. Connector hub base 331A, pierceable seal 356 sealing member 356A, and barrel lip 358A are secured in housing 352. Connector hub 331 further houses, in sterile chamber 332, stamped ring 391 fitted on seal mount 334 of connector hub 331; contact 392; spring 393; and interconnects 362 which are in communication with flexible power strip 394 (flex). As shown in FIG. 9A and FIG. 9B, in the initial state before activation of the drive, spring 393 rests in a non-compressed state, and contact 392 is held between spring 393 and stamped ring 391 in a position in which there is no contact between interconnects 362 and contact 392. Contact 392 is further stabilized within sterile chamber 332 by the position of piercing member 333 that passes through contact 392 through passage 392C.

Figures 9C, 9D:
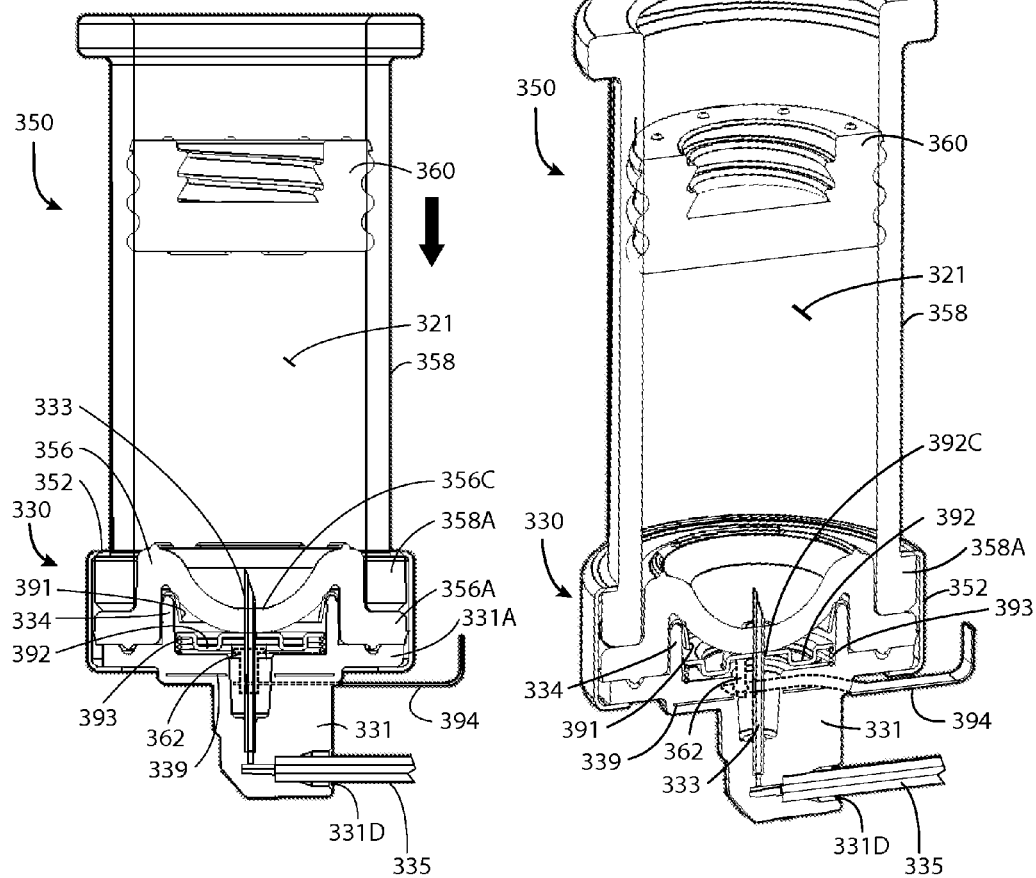
Figures 9E, 9F:
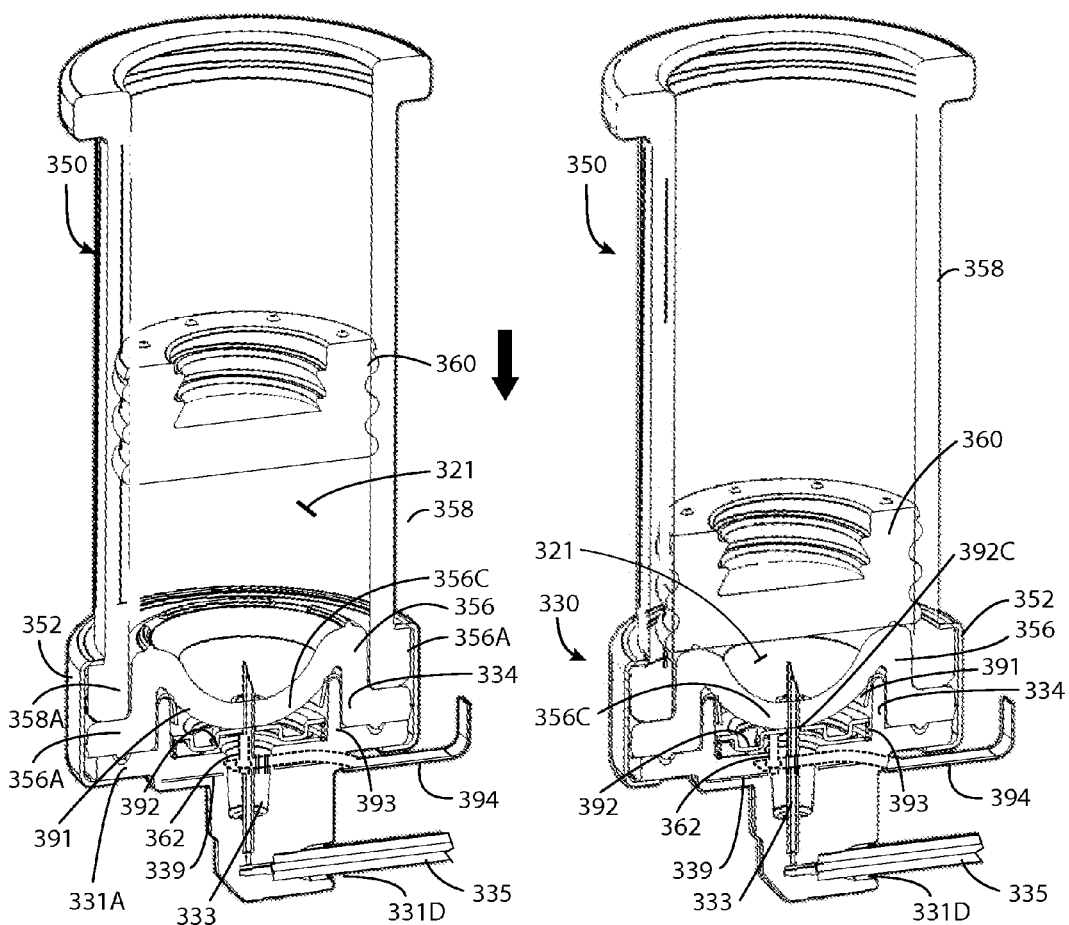
Figures 9G, 9H:
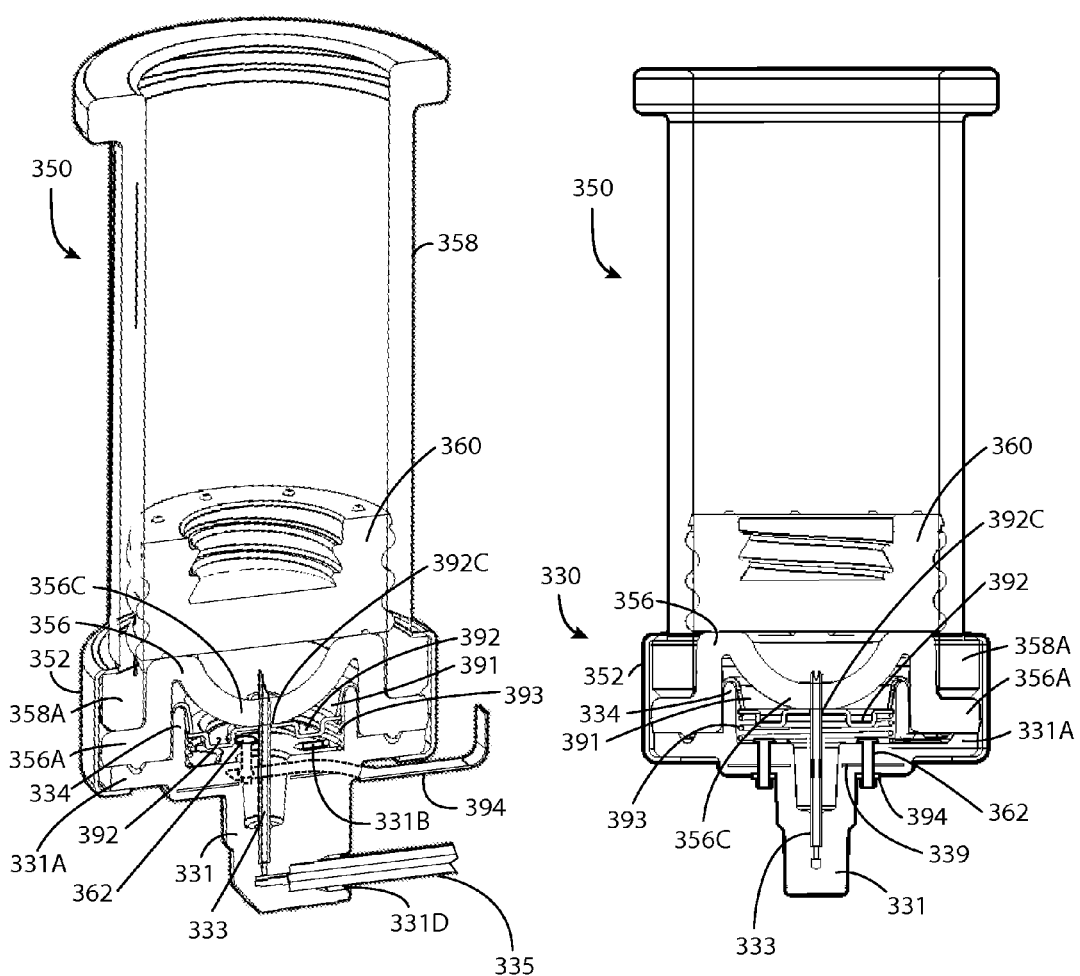

As shown in FIG. 9C and FIG. 9D, once the drive mechanism is activated and plunger seal 360 is forced toward piercing member 333, as indicated by the arrow, pneumatic and/or hydraulic pressure within mutable fluid chamber 321 forces seal barrier 356C of pierceable seal 356 into piercing member 333, thereby piercing seal barrier 356C and opening the sterile fluid pathway such that fluid can pass to sterile fluid conduit 335. This pneumatic and/or hydraulic pressure within mutable chamber 321 also forces at least a portion of barrier seal 356C against at least a portion of contact 392, such that spring 393 is compressed until contact 392 meets with interconnects 362 within sterile chamber 332, forming an interconnection. A signal can then be transduced via contact 392, interconnect 362, and flex 394. Continued pneumatic and/or hydraulic pressure (see arrow), as long as the drive is activated and fluid remains in mutable chamber 321, compresses spring 393 and maintains the contact between seal 356, contact 392 and interconnect 362, such that interconnection continues, as shown in FIG. 9E to FIG. 9F. When fluid has been pumped out of mutable fluid chamber 321, such that this chamber essentially no longer exists and flow through the sterile fluid connector 330 has ceased, as shown in FIG. 9G and FIG. 9H (the latter is a different sectional view of the sterile fluid pathway connector showing the position of interconnects 362 within connector hub 331), pneumatic and/or hydraulic pressure against seal 356 is released, and spring 393 returns to the non-compressed state, pushing contact 362 back toward stamped ring 391 and breaking interconnection between contact 392 and interconnect 362. Once this interconnection is broken, signal can no longer be transduced via flex 394.

Figure 10A:
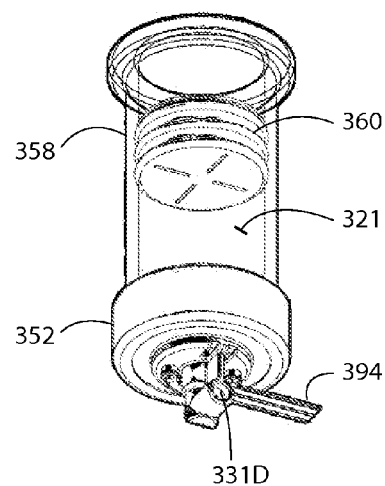
FIG. 10A to FIG. 10G are perspective and sectional views of another embodiment of a sterile fluid connector capable of transmitting a signal indicating the status of fluid transfer from the sterile fluid container to the connector.
Figure 10B:
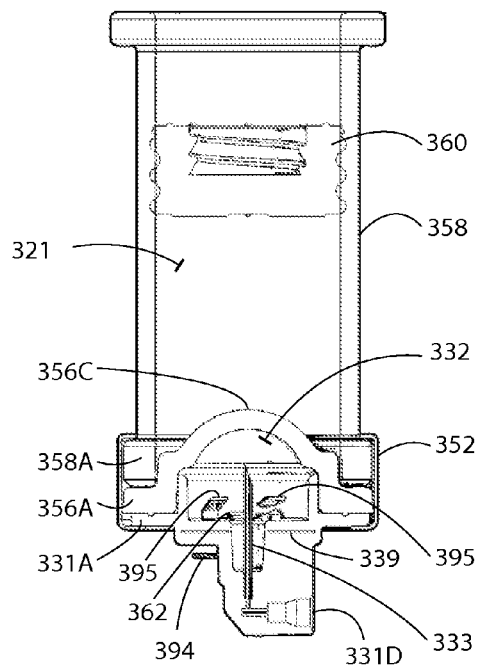
Figure 10C:
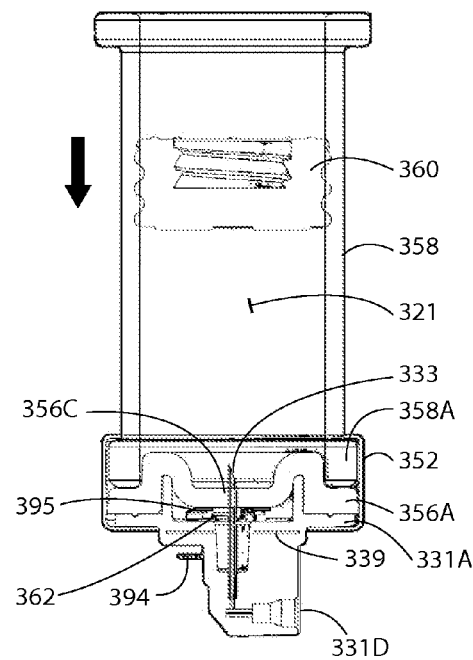
Figure 10D:
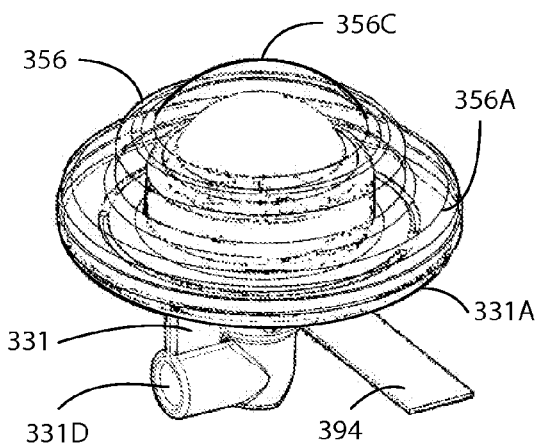
Figure 10E:
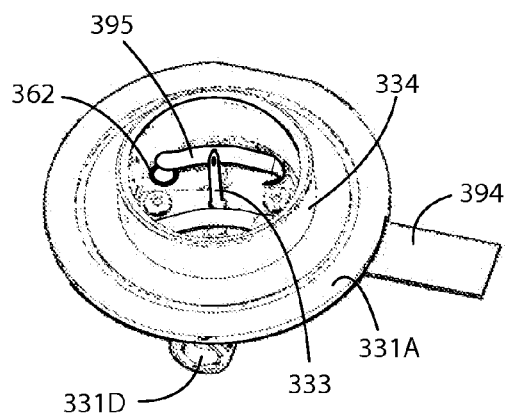
Figure 10F:
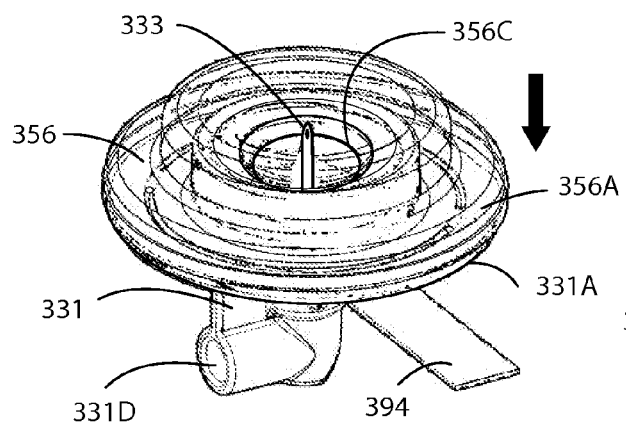
Figure 10G:
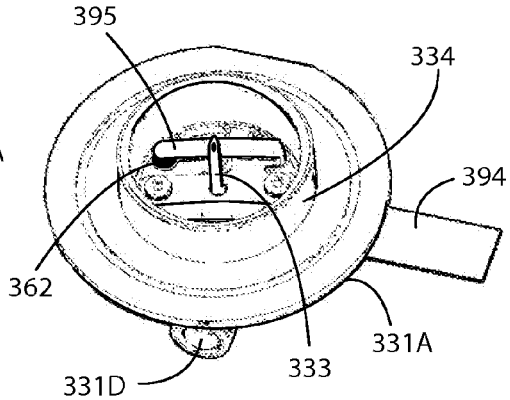

Other switch mechanisms can be designed that use the position of the membrane in pressured and unpressurized states to facilitate transduction of a signal to indicate the status of fluid transfer from the sterile fluid container to the connector. For example, as shown in FIG. 10A to FIG. 10G, connector hub 331 can house components of a switch comprising a leaf/flex arm contacts 395. FIG. 10B, FIG. 10D and FIG. 10E show the sterile fluid pathway connector in the pre-use position, in which pierceable seal 356 is unpierced and intact. In this position, contacts 395 are not touching (or in close enough proximity with) interconnects 362, and no signal can be transduced. FIG. 10C, FIG. 10F and FIG. 10G show the sterile fluid pathway connector in the activated, pressurized position, in which pneumatic and/or hydraulic pressure from the fluid chamber has deformed barrier seal 356C against piercing member 333, piercing pierceable seal 356 and opening the fluid pathway. In this position, barrier seal 356C has further been forced against contacts 395, such that contacts 395 meet (or become in close enough proximity) with interconnects 362, such that interconnection forms a signal that can be transduced via flex 394. FIGS. 10D and 10F are perspectives (in which the barrel and housing are not shown), that illustrate the positions of pierceable seal 356, connector hub 331, and piercing member 333 in pre-use and pressurized positions, respectively. FIGS. 10E and 10G are perspectives in which the barrel, housing and pierceable seal are not shown, to illustrate the positions of contacts 395 and interconnects 362 in pre-use (no interconnection) and pressurized (interconnected) positions, respectively.

Figure 11A:
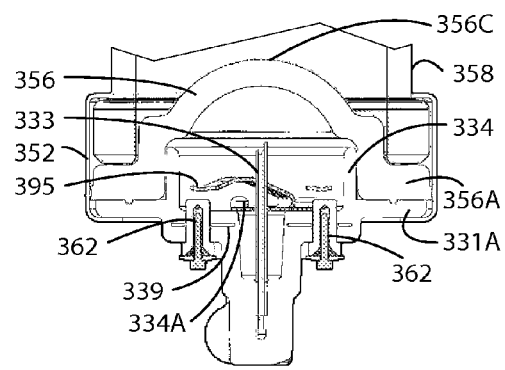
FIG. 11A to FIG. 11D are sectional and isomeric sectional views of another embodiment of a sterile fluid connector capable of transmitting a signal indicating the status of fluid transfer from the sterile fluid container to the connector, showing more specific configurations of a sensor in the open and closed positions.
Figure 11B:
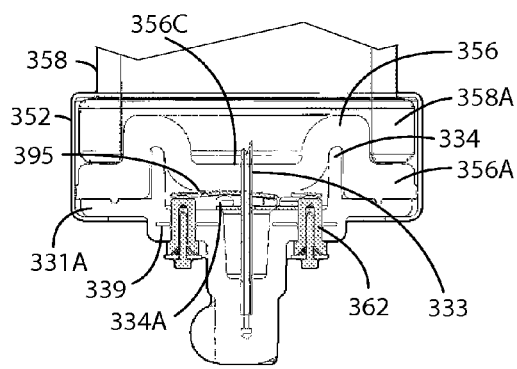
Figure 11C:
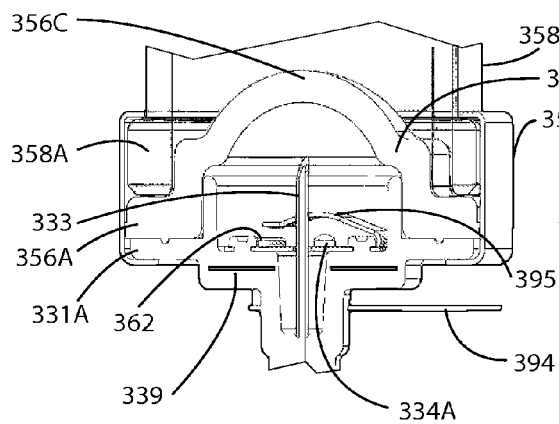
Figure 11D:
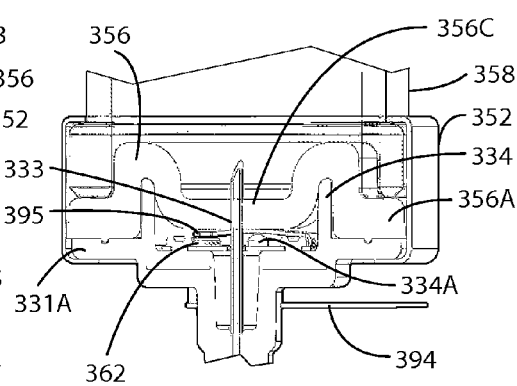

FIG. 11A to FIG. 11D further illustrate an embodiment in which leaf/arm contacts 395 do not form interconnection with interconnects 362 until and unless, as shown in FIG. 11B and FIG. 11D, pneumatic and/or hydraulic pressure force seal barrier 356C onto connects 395, which force then transferred to place contacts 395 in contact with interconnects 362, which then allows signal flow via flex 394. Additionally, as shown in the embodiment of FIG. 11A to FIG. 11D, connector hub 331 further includes internal post 334A, a structure that limits position of contacts 395 and membrane 356 to avoid an over-center position that might interfere with fluid passage through the sterile fluid pathway connector.

Figure 12A:
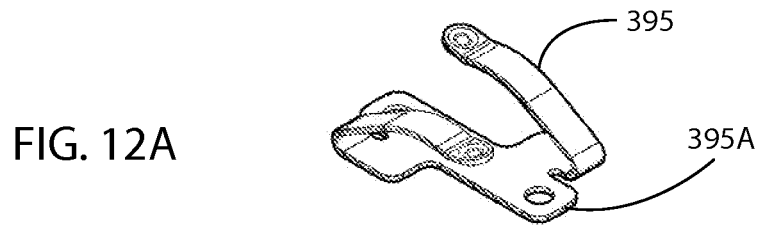
FIG. 12A to FIG. 12D are perspective and sectional views of an embodiment of a sterile fluid connector capable of transmitting a signal indicating the status of fluid transfer from the sterile fluid container to the connector, illustrating the unpressurized (FIG. 12B), pressurized (FIG. 12C), and end-of-delivery (FIG. 12D) positions of components of a sterile fluid connector.
Figure 12B:
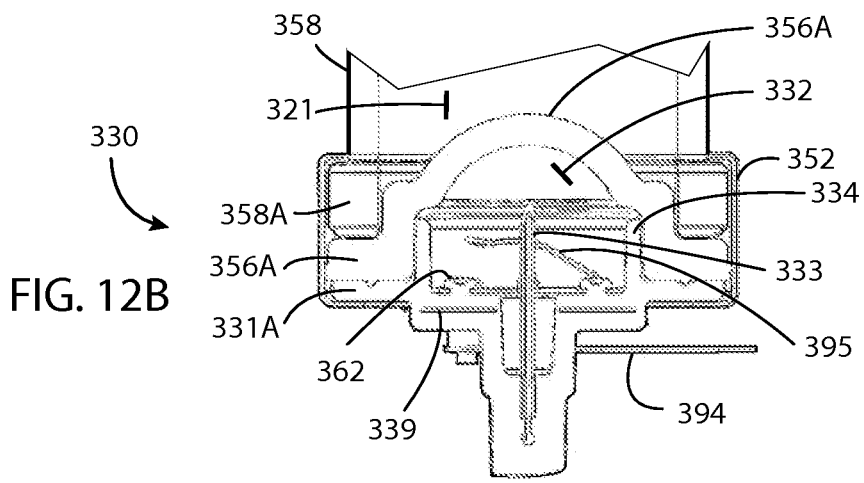
Figure 12C:
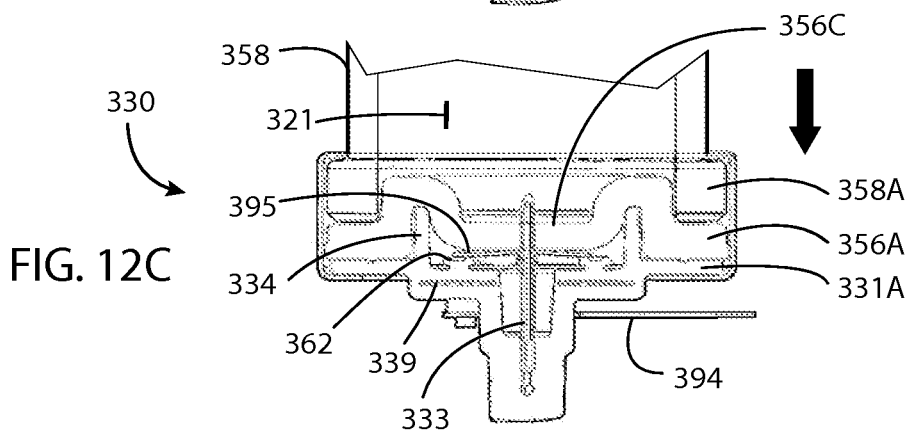
Figure 12D:
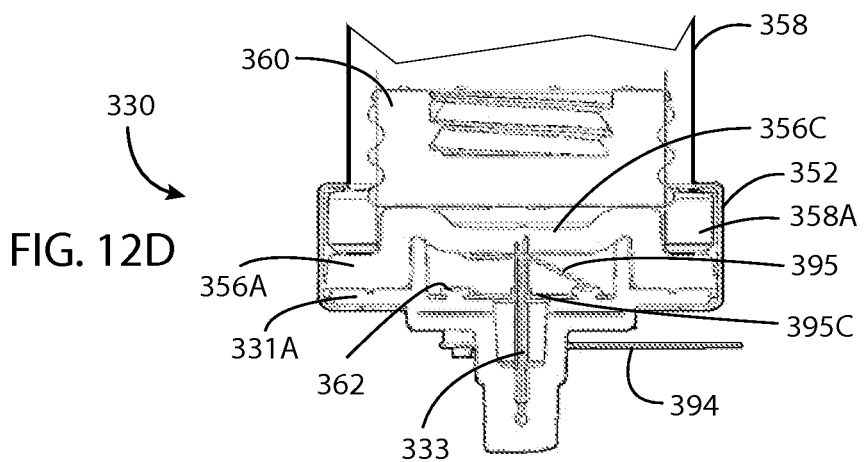
Figure 13A:
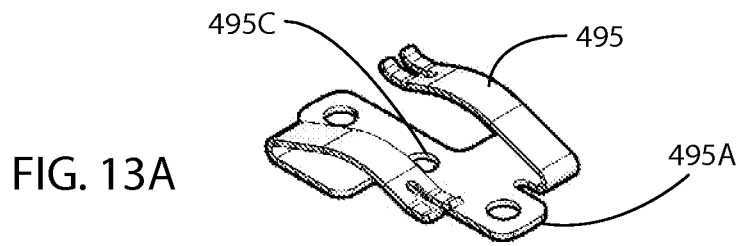
FIG. 13A to FIG. 13C are perspective and sectional views of another embodiment of a sterile fluid connector capable of transmitting a signal indicating the status of fluid transfer from the sterile fluid container to the connector.
Figure 13B:
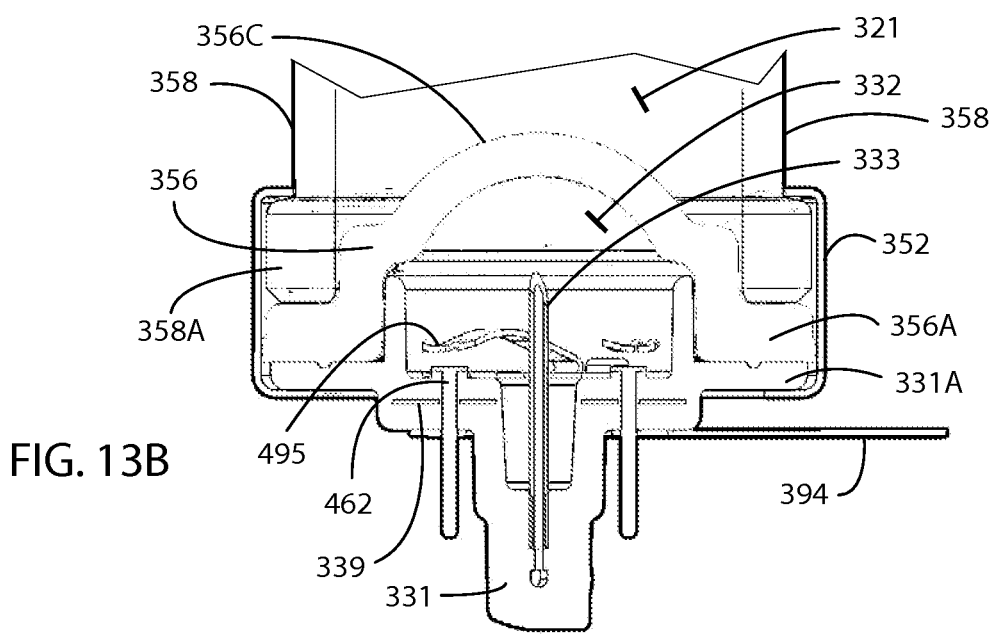
Figure 13C:
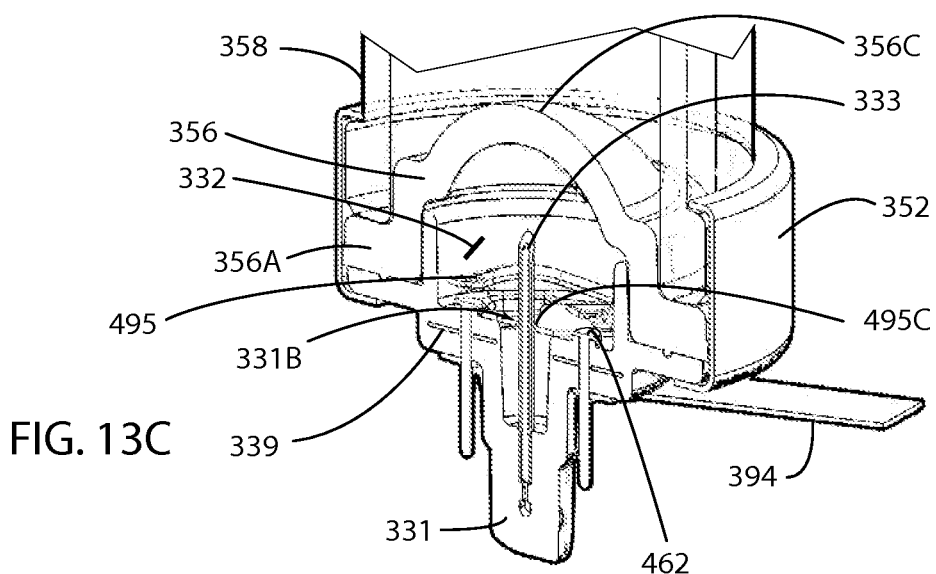

FIG. 12A to FIG. 12D further illustrate an embodiment of a sterile fluid connector capable of transmitting a signal indicating the status of fluid transfer from the sterile fluid container to the connector. FIG. 12B illustrates the position of components of a sterile fluid connector 330 in an unpressurized state, while FIG. 12C illustrates the pressurized state and FIG. 12D illustrates an end-of-delivery state. Interconnect(s) 362 and contact(s) 395 are situated within sterile chamber 332 between connector hub 331 and pierceable seal 356, such that after pierceable seal 356 is pierced, continued pressure within drug chamber 321 causes interconnection between one or more interconnect(s) 362 and one or more contact(s) 395, which transmits a signal to the user, and which signal is terminated once pressure inside the drug chamber 321 drops and interconnection is lost, i.e., at end-of-delivery. A number of known interconnects and contacts may be used with the present embodiments, which would readily be appreciated by a skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes. FIG. 13A to FIG. 13C illustrate another embodiment of a sterile fluid connector capable of transmitting a signal indicating the status of fluid transfer from the sterile fluid container to the connector.

Figure 14A:
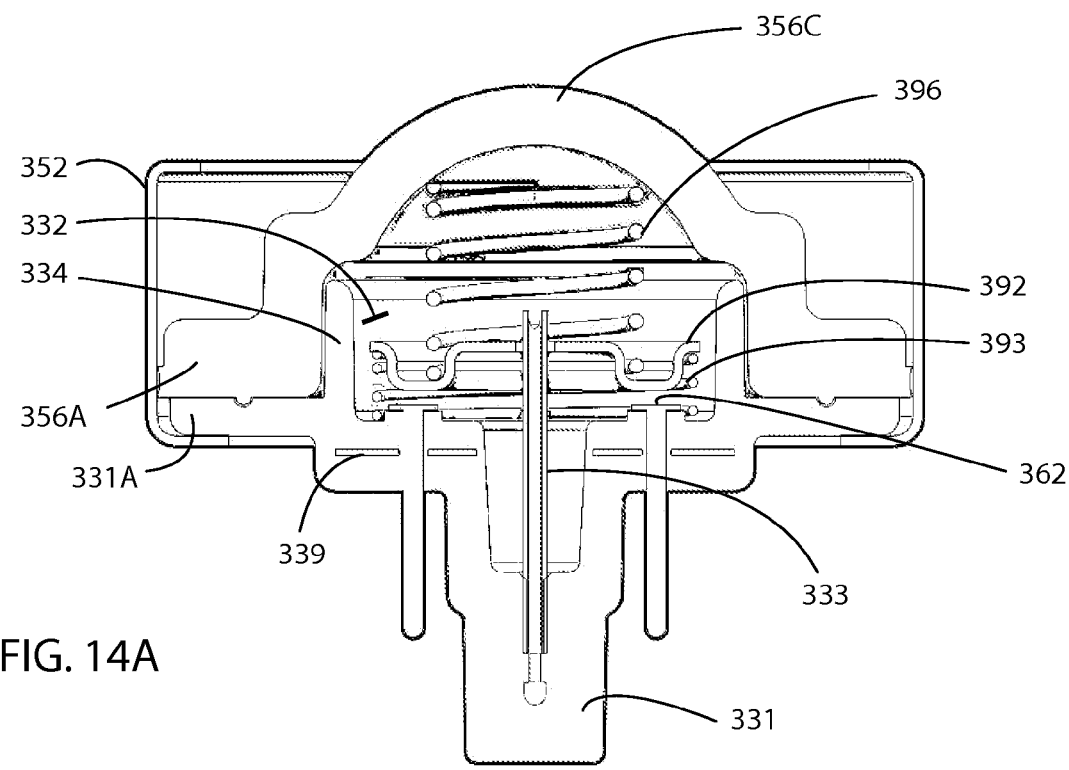
FIG. 14A is a sectional view.
Figure 14B:
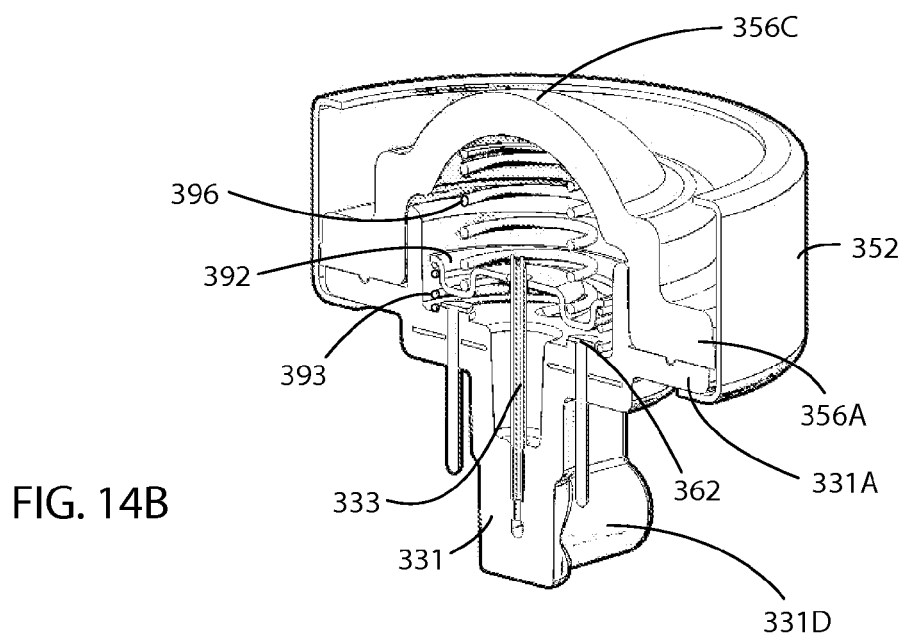
FIG. 14B is an isometric sectional view of another embodiment of a sterile fluid connector capable of transmitting a signal indicating the status of fluid transfer from the sterile fluid container to the connector.

Yet another switch mechanism is shown in FIG. 14A and FIG. 14B, which show sectional and sectional isometric views of a sterile fluid pathway connector (barrel not shown). In this embodiment, sterile chamber 332, defined in part by the position of pierceable seal 356 seal mount 334 and hub connection 331. Connector hub also holds piercing member 333 and interconnects 362 within the sterile chamber 332. The switch mechanism includes interconnects 362, first compression spring 393, contact 392, and second compression spring 396. In this embodiment, shown in the un-activated, depressurized state, both compression springs 393 and 396 compress in order for contact 392 to form an interconnection with interconnects 362. Before and upon release of pneumatic and/or hydraulic pressure against seal barrier 356, compression springs 393 and 396 decompress and interconnection is broken.

Figure 15A:
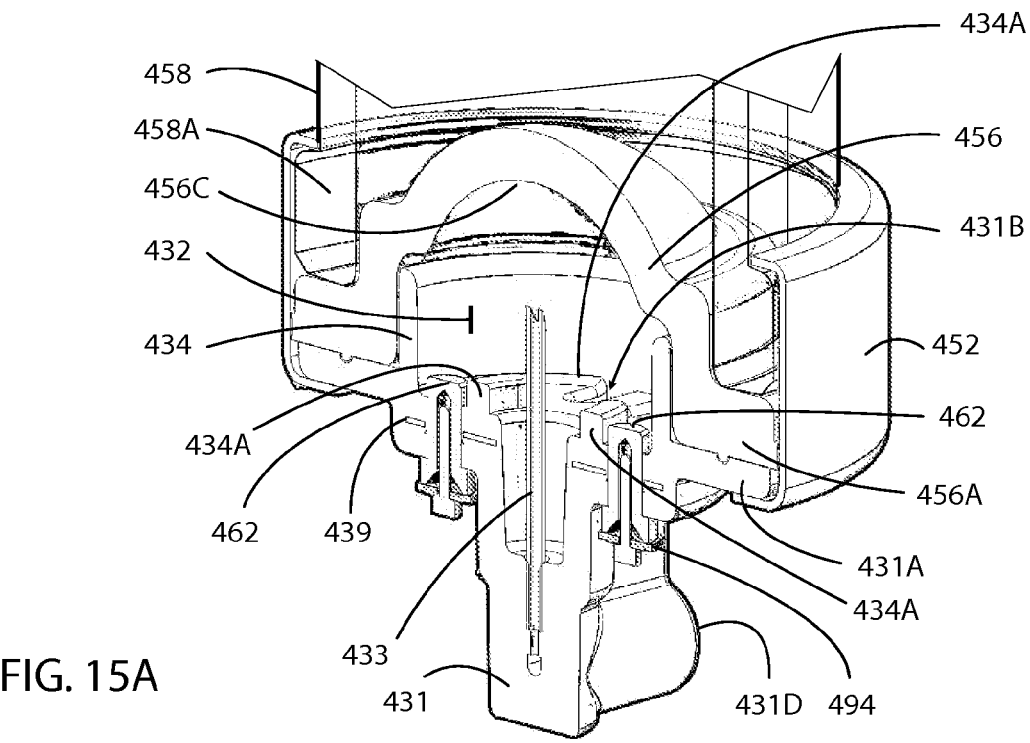
FIG. 15A and FIG. 15B are sectional isometric views of another embodiment of a sterile fluid connector capable of transmitting a signal indicating the status of fluid transfer from the sterile fluid container to the connector, in which the pierceable seal comprises a conductive material or coating.
Figure 15B:
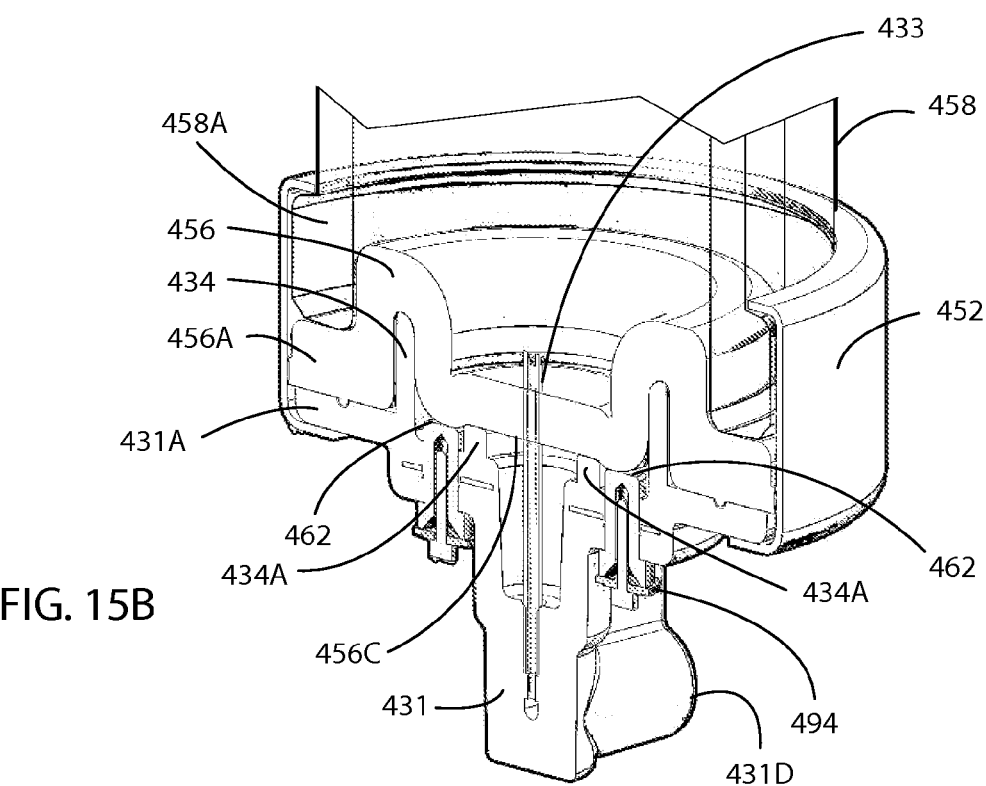

Another embodiment of a switch mechanism is shown in FIG. 15A and FIG. 15B. In this embodiment, pierceable seal 456 comprises a conductive material or coating. Connector hub 431 includes rib 434A, a structure that ensures that continuity between conductive pierceable seal 456 and contacts 462 is broken when system pressure drops at the end of fluid delivery. More specifically, as shown in FIG. 13B, in the pressurized system in which pneumatic and/or hydraulic pressure has caused conductive pierceable membrane 456 to have been ruptured by piercing member 433, conductive pierceable membrane 456 must deform further proximal to rib 434 in order to meet interconnects 462. Once pneumatic and/or hydraulic pressure ceases, i.e., at the end of fluid delivery, conductive pierceable membrane 456 is naturally released from interconnection by proximal to rib 434

Figure 16:
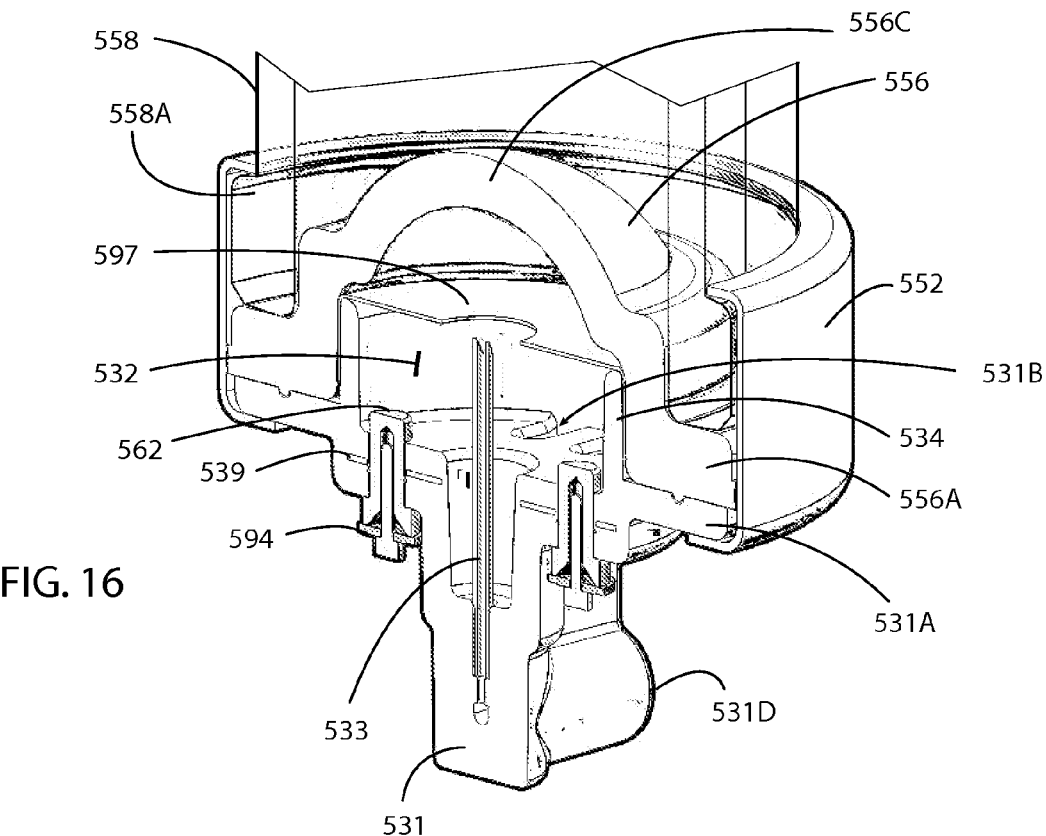
FIG. 16 is a sectional isometric view of another an embodiment of a sterile fluid connector capable of transmitting a signal indicating the status of fluid transfer from the sterile fluid container to the connector, in which signal is mediated using an conductive elastomeric film.

Yet another embodiment of a switch mechanism is shown in FIG. 16. In this embodiment, connector hub 531 comprises conductive elastomer 597 held in sterile chamber 532 between connector hub 531 and pierceable membrane 556. In this embodiment, at least a portion of conductive elastomer 597 is affixed to or otherwise engaged with seal mount 534, and is configured with a centrally located aperture to allow barrier seal 556C to be forced into contact with piercing member 533 upon activation of the pump and creation of pneumatic and/or hydraulic pressure against pierceable membrane 556. Conductive elastomer 597 is "springy" in nature and can deform (i.e., stretch) in response to distal force from pierceable seal 556, thereby deformed into meeting interconnects 362 under pressure from pierceable seal 356. The elastomeric nature of conductive elastomer 597 allows it to return to the pre-deformed state, in which there is no interconnection, in an unpressurized environment. Therefore, once pneumatic and/or hydraulic pressure ceases, i.e., at end-of-delivery, conductive elastomer film 597 is passively released from contact with interconnections 562, and signal is interrupted.

Figure 17:
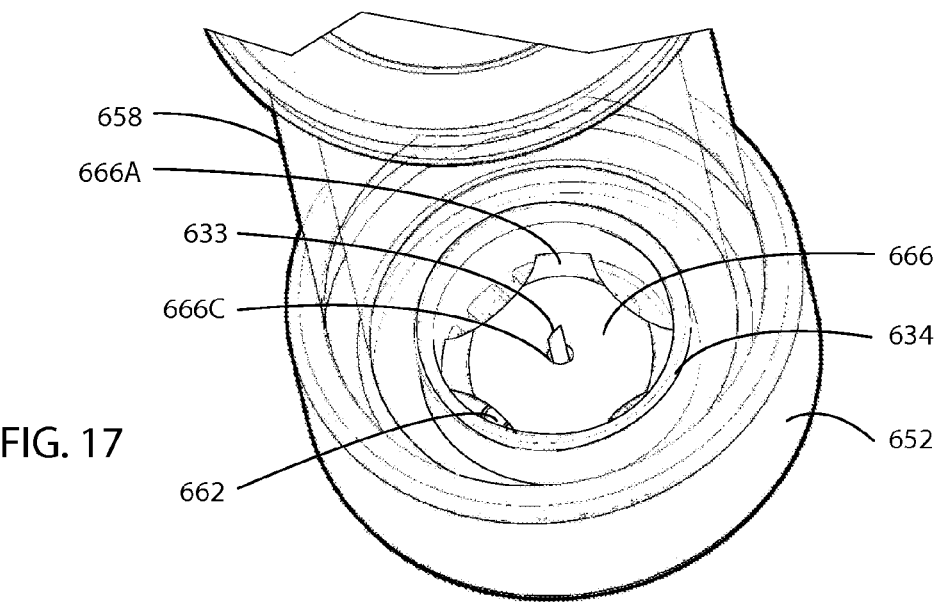
FIG. 17 is a sectional isometric view of another embodiment of a sterile fluid connector capable of transmitting a signal indicating the status of fluid transfer from the sterile fluid container to the connector, in which signal is mediated using a dome switch.

In another embodiment, shown in FIG. 17, the sterile fluid pathway connector includes a sensor mechanism comprising dome switch 666, which dome is made or of includes conductive material such that dome switch 666 can act as a contact to create a signal when dome switch 666 meets with, or moves sufficiently close to, interconnects 662 to complete the circuit. Dome switch 666 is configured with at least one outer portion 666A that resists deformation and engages with or bears against the inner wall of connector hub seal mount 634. Alternatively, the outer deformation-resistant portion of the dome switch can be a radial ring, or any structure that will stabilize the position of the dome within the sterile fluid pathway connector. The conductive portion of the dome switch may comprise shape-memory alloy that "remembers" its dome shape, but can be deformed into a more flattened shape under pressure, then return to the dome shape once pressure is relieved. In the embodiment of FIG. 17, dome switch 666 further comprises aperture 666C through which piercing member 633 can pass as dome switch 666 is pressed in the direction of interconnects 662. More specifically, when the pump device is actuated and pneumatic and/or hydraulic pressure builds against the pierceable membrane (not shown), the pierceable membrane is forced onto piercing member 633 and ruptured to open the fluid pathway. Dome switch 666 is similarly deformed by the pneumatic and/or hydraulic pressure or by the distal pressure of the deformed portion of the pierceable seal bearing against it, and dome switch 666 flattens towards interconnects 662 to allow a signal to be transduced. Once the pneumatic and/or hydraulic pressure stops, i.e., at end-of-delivery, the dome switch returns to its pre-deformed dome shape and interconnection ceases. As shown in FIG. 17, dome switch 666 is configured for placement under the pierceable seal (not shown), within the sterile cavity of the fluid pathway connector. The dome switch could, however, be configured to "ride" on top of the pierceable seal, and upon pressurization would be pushed in close enough proximity with interconnects 662 to generate a signal. Alternatively, the dome switch could be made of evenly deformable/resistant shape-memory material with the conductive portion of the dome switch configured in the outer portions or rim of the dome, and be placed "upside down" (as a bowl shape) in the sterile chamber of the fluid pathway connector. In this configuration, the pneumatic and/or hydraulic pressure against the pierced pierceable membrane would sufficiently flatten the dome until the outer conductive part of the dome made sufficient contact with interconnects positioned in the connector hub to allow a signal. Upon cessation of pressure, i.e., at end-of-delivery, the dome would pop back to its remembered dome shape, and thereby remove the connective contacts from interconnection.

As should be clear from the preceding discussions, a number of known interconnects and contacts, or similar components, are known in the art and may be utilized within the novel embodiments disclosed herein. As would readily be appreciated by one having skill in the art, a vast range of magnets, sensors, coils, and the like may be utilized to connect, transmit, or relay a signal for user feedback. Generally, any RLC circuit systems having a resistor, an inductor, and a capacitor, connected in series or in parallel, may be utilized for this purpose. For example, Hall effect sensors; giant magneto resistance (GMR) or magnetic field sensors; optical sensors; capacitive or capacitance change sensors; ultrasonic sensors; or linear travel, LVDT, linear resistive, or radiometric linear resistive sensors may be utilized as interconnects and corresponding contacts used to permit a signal to be sent to the power and control system to provide feedback to the user. The location of the contacts and interconnects may be interchanged or in a number of other configurations which permit completion of an electrical circuit or otherwise permit a transmission between the components. By use of one or more status switch interconnects and one or more corresponding electrical contacts, the status of the drive mechanism before, during, and after operation can be relayed to the power and control system to provide feedback to the user. Such feedback may be tactile, visual or auditory, and may be redundant such that more than one signals or types of feedback are provided to the user during use of the device.

Additionally, the embodiments of the present invention provide end-of-delivery compliance to ensure that substantially the entire fluid volume has been delivered and that the status indication features have been properly contacted to provide accurate feedback to the user. Through these mechanisms, confirmation of fluid delivery can accurately be provided to the user or administrator. Accordingly, the novel devices of the present invention alleviate one or more of the problems associated with prior art devices. Optionally, the drive mechanism may include one or more compliance features that enable additional axial translation of the plunger seal to, for example, ensure that substantially the entire fluid volume has been delivered and make sure that the feedback contact mechanisms have connected. For example, in one embodiment of the present invention, the drive mechanism may be configured to drive further axial translation of at least a portion of the plunger seal for a compliance push of the plunger seal, or of fluid, from the fluid container. Additionally or alternatively, the plunger seal, itself, may have some compressibility permitting a compliance push. For example, when a pop-out plunger seal is employed, i.e., a plunger seal that is deformable from an initial state, the plunger seal may be caused to deform or "pop-out" to provide a compliance push. Similarly, the plunger seal may be porous, compressible, deformable, or the like to itself be capable of providing a compliance push.

As described above, the location of the contacts and interconnects may be interchanged or in a number of other configurations that permit completion of an electrical circuit or otherwise permit a transmission between the components. In one embodiment, the plunger seal may incorporate, or itself be utilized as, a contact or interconnect for the status indication mechanism (e.g., 61 in FIG. 4C). In one embodiment, the seal mount may incorporate, or itself be utilized as, a contact or interconnect for the status indication mechanism (e.g., 62 in FIG. 4C). In one embodiment, a guide piece may incorporate, or itself be utilized as, a contact or interconnect for the status indication mechanism (e.g., 232 in FIG. 6A). In another embodiment, the proximal surface of the connector hub sequestered in sterile chamber 32 may incorporate, or itself be utilized as, a contact or interconnect for the status indication mechanism (e.g., FIG. 9 to FIG. 17).

Other components of the sterile fluid pathway connection may similarly be utilized for multiple functions. Alternatively, other optional components may be utilized within the novel embodiments of the present invention. For example, one or more optional flow restrictors may be utilized within the configurations of the fluid pathway connection described herein. In at least one embodiment, a flow restrictor may be utilized at the connection between the piercing member and the fluid conduit. The fluid pump is capable of delivering a range of fluid with different viscosities and volumes. The fluid pump is capable of delivering a fluid at a controlled flow rate (speed) or of a specified volume. In one embodiment, the fluid delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the fluid container to dispense the fluid therein, or combinations thereof. In at least one embodiment of the present invention, the connector hub itself may be utilized as part of the fluid path and may, optionally, function as a flow restrictor.

It will be appreciated from the above description that the fluid pathway connections and fluid pumps disclosed herein provide an efficient and easily-operated system for automated fluid delivery from a fluid container. The novel devices of the present invention provide container connections which maintain the sterility of the fluid pathway and which are integrated into the fluid container, and fluid delivery pumps that incorporate such integrated sterile fluid pathway connections to fluid containers. Such devices are safe and easy to use, and are aesthetically and ergonomically appealing for self-administering patients. The devices described herein incorporate features which make activation, operation, and lock-out of the device simple for even untrained users. Because the fluid path is disconnected until fluid delivery is desired by the operator, the sterility of the fluid pathway connection, the fluid container, the fluid, and the device as a whole is maintained. These aspects of the present embodiments provide highly desirable storage, transportation, and safety advantages to the operator. Furthermore, the novel configurations of the fluid pathway connections and drug pumps of the present invention maintain the sterility of the fluid path through operation of the device. Because the path that the fluid travels within the device is entirely maintained in a sterile condition, only these components need be sterilized during the manufacturing process. Such components include the fluid container of the drive mechanism, the fluid pathway connection, the sterile fluid conduit, and, when the fluid is a drug, the insertion mechanism. In at least one embodiment of the present invention, the power and control system, the assembly platform, the control arm, the activation mechanism, the housing, and other components of the fluid pump do not need to be sterilized. This greatly improves the manufacturability of the device and reduces associated assembly costs. Accordingly, the devices of the present invention do not require terminal sterilization upon completion of assembly. A further benefit of the present embodiments is that the components described herein are designed to be modular such that, for example, the fluid pathway connection and other components of the device may be integrated into a housing and readily interface to function as a fluid pump.

Assembly or manufacturing of fluid pathway connection 30, fluid delivery pump 100, or any of the individual components may utilize a number of known materials and methodologies in the art. For example, a number of known cleaning fluids such as isopropyl alcohol and hexane may be used to clean the components or the devices. A number of known adhesives may similarly be employed in the manufacturing process. Additionally, known siliconization or lubrication fluids and processes may be employed during the manufacture of the novel components and devices. Furthermore, known sterilization processes may be employed at one or more of the manufacturing or assembly stages to ensure the sterility of the final product.

The fluid pathway connection may be assembled in a number of methodologies. In one method of assembly, the sterile fluid pathway connection may be assembled, e.g., as shown in FIG. 5A and FIG. 5B, and then attached, mounted, connected, or otherwise integrated into fluid container 50 such that at least a portion of the pierceable seal 56 is contained within the fluid container 50. The fluid container 50 may then be filled with a fluid and plugged with a plunger seal 60 at an end opposite the pierceable seal 56. The barrel 58 may be filled with a fluid through the open proximal end prior to insertion of the plunger seal 60 from the proximal end of the barrel 58. The drive mechanism 90 may then be attached to the proximal end of the fluid container 50 such that a component of the drive mechanism 90 is capable of contacting the plunger seal 60. The insertion mechanism 70 may be assembled and attached to the other end of the fluid conduit 35. This entire sub-assembly, including drive mechanism 90, fluid container 50, fluid pathway connection 30, fluid conduit 35, and insertion mechanism 70, may be sterilized by known techniques before assembly into the fluid pump 100. Certain components of this sub-assembly may be mounted to an assembly platform within the housing 12A, 12B or directly to the interior of the housing 12A, 12B, while other components may be mounted to a guide, channel, or other component or aspect for activation by the user.

Manufacturing of a fluid pump includes the step of attaching both the fluid pathway connection and fluid container, either separately or as a combined component, to an assembly platform or housing of the drug pump. The method of manufacturing further includes attachment of the drive mechanism, fluid container, and insertion mechanism to the assembly platform or housing. The additional components of the fluid pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the fluid pump includes one or more of the following steps: activating, by a user, the activation mechanism; displacing a control arm to actuate an insertion mechanism; activating a drive control mechanism to push the plunger seal, connect the sterile fluid pathway connection, and drive fluid flow through the fluid pump, wherein translating the fluid pathway connection causes a pierceable seal to be pierced by a piercing member thereby opening a fluid path from the fluid container to the fluid pathway connection. The drive control mechanism may be activated by actuating a power and control system. The method may further include the step of: engaging an optional on-body sensor prior to activating the activation mechanism. Furthermore, the method of operation may include translating a plunger seal within the drive control mechanism and fluid container to force fluid drug flow through the fluid container, the fluid pathway connection, a sterile fluid conduit, and, optionally the insertion mechanism for delivery of the fluid to the body of a user.

Throughout the specification, the aim has been to describe the preferred embodiments of the invention without limiting the invention to any one embodiment or specific collection of features. Various changes and modifications may be made to the embodiments described and illustrated without departing from the present invention.

We claim:

1. A sterile fluid pathway assembly comprising
a sterile fluid container;
a sterile fluid conduit; and
a sterile fluid connector comprising
a first portion configured to connect the sterile fluid conduit; and
a second portion configured to mount the sterile fluid container;
a connector hub;
a pierceable seal disposed at least partially between the connector hub and a sterile fluid chamber of the sterile fluid container, the pierceable seal in sealing contact with the connector hub to form a sterile cavity between the connector hub and the pierceable seal; and
a piercing member fixedly disposed within the connector hub capable of providing a sterile fluid communication between the sterile fluid chamber and the sterile fluid conduit;
wherein at least a portion of the pierceable seal is configured to transform from a non-activated state wherein the pierceable seal is intact, to an activated state wherein the pierceable seal is disrupted by the piercing member to create a sterile fluid communication between the sterile fluid chamber of the sterile fluid container and the sterile fluid conduit; and
wherein the sterile fluid container comprises a plunger seal and translation of the plunger seal results in relative motion of the pierceable seal and the piercing member.

2. The sterile fluid pathway assembly of claim 1, wherein the pierceable seal is further configured to recess a portion of the sterile cavity within the sterile fluid container.

3. The sterile fluid pathway assembly of claim 1, wherein the connector hub further comprises at least one port.

4. The sterile fluid pathway assembly of claim 1, wherein the plunger seal is configured to engage the connector hub in the activated state to minimize residual fluid in the sterile fluid container.

5. An infusion pump device comprising
an insertion mechanism; and
a sterile fluid pathway assembly comprising
a sterile fluid container;
a sterile fluid conduit; and
a sterile fluid connector comprising
a first portion configured to connect the sterile fluid conduit; and
a second portion comprising a housing configured to mount a sterile fluid container;
a connector hub;
a pierceable seal disposed at least partially between the connector hub and a sterile fluid chamber of the sterile fluid container, the pierceable seal in sealing contact with the connector hub to form a sterile cavity between the connector hub and the pierceable seal; and
a piercing member fixedly disposed within the connector hub, capable of providing a sterile fluid communication between the sterile fluid chamber and the sterile fluid conduit;
wherein at least a portion of the pierceable seal is configured to transform from a non-activated state wherein the pierceable seal is intact, to an activated state wherein the pierceable seal is disrupted by the piercing member to create a sterile fluid communication between the sterile fluid chamber of the sterile fluid container and the sterile fluid conduit; and
wherein the sterile fluid container comprises a plunger seal and translation of the plunger seal results in relative motion of the pierceable seal and the piercing member;
wherein actuation of the drive mechanism causes fluid movement from the sterile fluid container through the sterile fluid pathway assembly to the insertion mechanism.

6. The infusion pump device of claim 5, wherein the pierceable seal is further configured to recess a portion of the sterile cavity within the sterile fluid container.

7. The infusion pump device of claim 5, wherein the connector hub of the sterile fluid connector further comprises at least one port.

8. The infusion pump device of claim 5, wherein the plunger seal is configured to engage the connector hub in the activated state to minimize residual fluid in the sterile fluid container.

9. The sterile fluid pathway assembly of claim 1, wherein relative motion of the pierceable seal and the piercing member causes the pierceable seal to transform from the non-activated state to the activated state.

10. The sterile fluid pathway assembly of claim 1, wherein the position of at least a portion of the pierceable seal is fixed with respect to the sterile fluid container.

11. The sterile fluid pathway assembly of claim 1, wherein a portion of the pierceable seal abuts an end of the sterile fluid container.

12. The infusion pump of claim 5, wherein relative motion of the pierceable seal and the piercing member causes the pierceable seal to transform from the non-activated state to the activated state.

13. The infusion pump of claim 5, wherein the position of at least a portion of the pierceable seal is fixed with respect to the sterile fluid container.

* * * * *